United States Patent
Welch et al.

(10) Patent No.: US 11,422,403 B2
(45) Date of Patent: Aug. 23, 2022

(54) SQUARYLIUM COMPOUNDS FOR USE IN DISPLAY DEVICES

(71) Applicant: NITTO DENKO CORPORATION, Osaka (JP)

(72) Inventors: Michael Welch, San Diego, CA (US); Shijun Zheng, San Diego, CA (US); Peng Wang, San Diego, CA (US)

(73) Assignee: NITTO DENKO CORPORATION, Osaka (JP)

( * ) Notice: Subject to any disclaimer, the term of this patent is extended or adjusted under 35 U.S.C. 154(b) by 129 days.

(21) Appl. No.: 16/767,056

(22) PCT Filed: Nov. 27, 2018

(86) PCT No.: PCT/US2018/062629
§ 371 (c)(1),
(2) Date: May 26, 2020

(87) PCT Pub. No.: WO2019/108544
PCT Pub. Date: Jun. 6, 2019

(65) Prior Publication Data
US 2020/0369889 A1 Nov. 26, 2020

Related U.S. Application Data

(60) Provisional application No. 62/672,956, filed on May 17, 2018, provisional application No. 62/592,223, filed on Nov. 29, 2017.

(51) Int. Cl.
*C09B 57/00* (2006.01)
*G02B 5/22* (2006.01)
(Continued)

(52) U.S. Cl.
CPC ..... *G02F 1/133528* (2013.01); *C07D 207/00* (2013.01); *C07D 207/44* (2013.01); *C07D 209/00* (2013.01); *C07D 209/60* (2013.01); *C07D 403/00* (2013.01); *C07D 403/08* (2013.01); *C09B 57/007* (2013.01); *C09J 7/10* (2018.01); *C09J 7/20* (2018.01); *C09J 7/385* (2018.01); *C09J 11/06* (2013.01); *G02B 1/10* (2013.01); *G02B 5/223* (2013.01); *G02F 1/133302* (2021.01); *G02F 1/133509* (2013.01); *G02F 1/133533* (2013.01); *G02F 1/133536* (2013.01); *G02F 1/133634* (2013.01); *H01L 33/50* (2013.01); *C09J 2203/318* (2013.01); *C09J 2301/302* (2020.08);
(Continued)

(58) Field of Classification Search
CPC .............................. C09B 57/007; G02B 5/223
See application file for complete search history.

(56) References Cited

U.S. PATENT DOCUMENTS 4,353,971 A 10/1982 Chang et al.
4,743,530 A 5/1988 Farid et al.
(Continued)

FOREIGN PATENT DOCUMENTS

DE 10245581 A1 10/2003
JP 2001183522 A1 7/2001
(Continued)

OTHER PUBLICATIONS

Leigh, D.A. et al., The Mechanism of Formation of Amide-Based Interlocked Compounds: Prediction of a New Rotaxane-Forming Motif, Chem. Eur. J., 10(20), 4960-4969, bearing an alleged date of Oct. 2004.
(Continued)

*Primary Examiner* — Kristin A Vajda
(74) *Attorney, Agent, or Firm* — Maschoff Brennan; Brent Johnson; David W. Old

(57) ABSTRACT

Described herein are embodiments of squarylium compounds for use as filters in light-emitting and/or display devices. One problem of known quarylium dyes is that strong nucleophiles can attack the electron-deficient cyclobutene ring which can lead to a loss of the dye's colour. Another potential drawback with squaraine dyes can be their tendency to form aggregates, which can lead to a substantial broadening of their absorption bands. Use of the present compounds in filters address these problems. The squarylium compounds of the present invention have the following formulas:

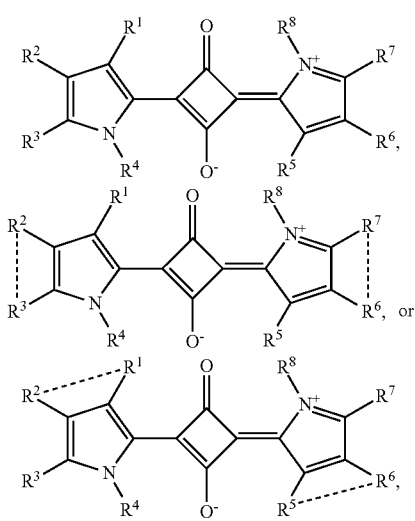

15 Claims, 4 Drawing Sheets

(51) Int. Cl.
    *G02F 1/1335*         (2006.01)
    *C07D 403/08*        (2006.01)
    *H01L 33/50*         (2010.01)
    *G02F 1/13363*       (2006.01)
    *C07D 207/44*        (2006.01)
    *C07D 209/60*        (2006.01)
    *C07D 207/00*        (2006.01)
    *C07D 209/00*        (2006.01)
    *C07D 403/00*        (2006.01)
    *C09J 7/38*           (2018.01)
    *C09J 7/10*           (2018.01)
    *C09J 11/06*         (2006.01)
    *C09J 7/20*           (2018.01)
    *G02F 1/1333*        (2006.01)
    *G02B 1/10*          (2015.01)

(52) U.S. Cl.
    CPC .... *C09J 2301/312* (2020.08); *C09J 2301/408* (2020.08); *C09J 2429/008* (2013.01); *C09J 2433/00* (2013.01); *C09K 2323/03* (2020.08); *C09K 2323/031* (2020.08); *G02F 1/133541* (2021.01); *G02F 1/133638* (2021.01); *G02F 2202/28* (2013.01)

(56) References Cited

U.S. PATENT DOCUMENTS

| | | | |
|---|---|---|---|
| 6,157,504 | A | 12/2000 | Yamada et al. |
| 6,638,624 | B2 | 10/2003 | Ozawa |
| 6,746,629 | B2 | 6/2004 | Ozawa et al. |
| 6,836,383 | B1 | 12/2004 | Ozawa et al. |
| 8,273,875 | B2 | 9/2012 | Smith et al. |
| 8,642,014 | B2 | 2/2014 | Terpetschnig et al. |
| 8,703,296 | B2 | 4/2014 | Fujinaka et al. |
| 2005/0142489 | A1 | 6/2005 | Berneth et al. |
| 2007/0281363 | A1 | 12/2007 | Patsenker et al. |
| 2008/0166650 | A1 | 7/2008 | Hasegawa et al. |
| 2009/0247769 | A1 | 10/2009 | Ito et al. |
| 2012/0296085 | A1 | 11/2012 | Smith |
| 2014/0198285 | A1 | 7/2014 | Fujita et al. |

FOREIGN PATENT DOCUMENTS

| | | |
|---|---|---|
| JP | 2008-184606 A | 8/2008 |
| JP | 2016079144 A | 5/2016 |
| JP | 2016079331 A | 5/2016 |
| JP | 2017141215 A | 8/2017 |
| JP | 2017141425 A | 8/2017 |
| JP | 2017203902 A | 11/2017 |
| JP | 2018045011 A | 3/2018 |
| WO | 2016120166 A1 | 8/2016 |

OTHER PUBLICATIONS

Arunkumar, E. et al., Squaraine-Derived Rotaxanes: Sterically Protected Fluorescent Near-IR Dyes, Journal of the American Chemical Society, 127(10), 3288-3289, bearing an alleged date of Mar. 2005.

Lynch D.E., Pyrrolyl Squaraines—Fifty Golden Years, Metals, 5(3), 1349-1370, bearing an alleged date of Sep. 2015.

Ahn, H.-Y. et al., Near-Infrared Emitting Squaraine Dyes with High 2PA Cross Sections for Multiphoton Fluorescence Imaging, ACS Applied Materials & Interfaces, 4(6), 2847-2854, bearing an alleged date of Jun. 2012.

Paek, S. et al., Efficient and stable panchromatic squaraine dyes for dye-sensitized solar cells, Chemical Communications, 47(10), 2874-2876, bearing an alleged date of 2011.

Chenthamarakshan, C.R. et al., Synthesis and Properties of Water-Soluble Squaraine Oligomers Containing Pendant Propanesulfonate Moieties, Chemistry of Materials, 10(6), 1657-1663, bearing an alleged date of Jun. 1998.

Lynch, D., et al., Synthesis and non-linear optical properties of (N-alkylpyrrol-2-yl) squaraine derivatives. Part 2, Journal of the Chemical Society, Perkin Transactions 2, 4, 779-784, bearing an alleged date of 1998.

Treibs, A. et al., Cyclobutenderivate der Pyrrolreihe, Justus Liebigs Annalen der Chemie, 699(1), 153-167, bearing an alleged date of 1966.

Bonnett, R. et al., Squaraines based on 2-arylpyrroles, Tetrahedron, 60(40), 8913-8918, bearing an alleged date of Sep. 2004.

International Search Report and Written Opinion, PCT/US2018/062629, dated May 28, 2019.

Office Action in corresponding Korean application, 10-2020-7018376, dated Mar. 14, 2022; English machine translation also attached.

SQUARYLIUM COMPOUNDS FOR USE IN DISPLAY DEVICES

CROSS-REFERENCE TO RELATED APPLICATIONS

This application is a national phase application of PCT/US2018/062629, filed Nov. 27, 2018, which claims the benefit of U.S. Provisional Application Nos. 62/592,223, filed Nov. 29, 2017, and 62/672,956, filed May 17, 2018, the contents of which are incorporated herein by reference in its entirety.

BACKGROUND

Field

The embodiments include squarylium compounds for use in filters for use in conjunction with light-emitting/display devices.

Description of the Related Art

In color reproduction, an entire range of colors, or color gamut, can be a given complete subset of colors. The most common usage refers to the subset of colors which can be accurately represented in a given circumstance, such as by a certain output device. For example, the wide-gamut Red Green Blue (RGB) color space (or Adobe Wide Gamut RGB) is an RGB color space developed by Adobe Systems, which offers a large gamut by using pure spectral primary colors. It is asserted to be able to store a wider range of color values than sRGB or Adobe RGB color spaces. So, it is believed, that a display device which could provide a wider gamut could enable the device to portray more vibrant colors. However, when providing these colors, the portrayal of the green and red colors can be spectrally adjacent to each other and not fully distinguishable from each other. One way to reduce these color aberrations can be to utilize an absorbing dye to reduce the amount of spectral emission and overlap in this region. In some cases, an absorbing dye having an absorption wavelength between about 580 nm to about 620 could be useful. In addition, to reduce the effect of the removal of emitted light while sharpening the distinction between the perceived green and red colors, a narrow absorption spectrum, as indicated by a narrow full width half maximum (FWHM) can be desirable.

SUMMARY

The squaraines are a class of Near-Infra Red (IR) dyes. Squaraines are also referred to as squarylium compounds, squarylium dyes and squaraine dyes and are prepared from squaric acid. They can be useful in conjunction with color displays, wherein the dye can be useful as a sharp minimum value absorption filter in the wavelength region of 480 nm to 520 nm. However, there are several problems with these compounds, e.g., they do not have an absorption wavelength between about 580 nm to about 620 nm and/or do not have a narrow full width half maximum.

One problem is that strong nucleophiles can attack the electron-deficient cyclobutene ring which can lead to a loss of the dye's color. Another potential drawback with squaraine dyes can be their tendency to form aggregates, which can lead to a substantial broadening of their absorption bands.

Thus, there is a need for a stable squaraine compound having desired characteristics.

Described herein are embodiments of squarylium compounds for use as filters in light-emitting and/or display devices. Use of these compounds in filters may help to address some of the problems described above. Some embodiments can include one or more squaraine compounds for use in filter elements, emissive elements of organic light emitting devices and/or emissive elements in display devices.

Some embodiments include a squarylium compound of the following formula:

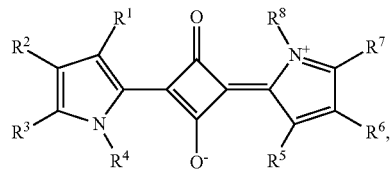

wherein $R^1$, $R^2$, $R^3$, $R^5$, $R^6$, and $R^7$ are independently H, halogen, optionally substituted $C_{1-24}$ hydrocarbyl, optionally substituted —S-hydrocarbyl, or optionally substituted —O-hydrocarbyl. In some embodiments, $R^4$ and $R^8$ are independently H or optionally substituted $C_{1-24}$ hydrocarbyl. In some embodiments, the optionally substituted $C_{1-24}$ hydrocarbyl can be optionally substituted benzyl, optionally substituted ethylphenyl, or optionally substituted propylphenyl. In some embodiments, ethylphenyl refers to —$CH_2CH_2Ph$. In some embodiments, the compound can be any or all of the structures described later herein. In some embodiments, at least one of $R^1$ and $R^2$, $R^2$ and $R^3$, $R^5$ and $R^6$, or $R^6$ and $R^7$ can be covalently bound together to form another ring. In some embodiments, the ring system can be a cyclohexapyrrolyl (tetrahydroindolyl) ring. In some embodiments, the ring system can be a cyclopentapyrrolyl ring. In some embodiments, the ring system can be a cycloheptapyrrolyl ring. In some embodiments, the ring system can be a dihydrobenzoindolyl ring. In some embodiments, the compound can be selected from specific structures described later herein.

Some embodiments can include a filter comprising a compound described above. Some embodiments can include a display device described above comprising a filter wherein the filter is comprised of a squarylium compound described above.

These and other embodiments are described in greater detail below.

DETAILED DESCRIPTION

Figure 1:
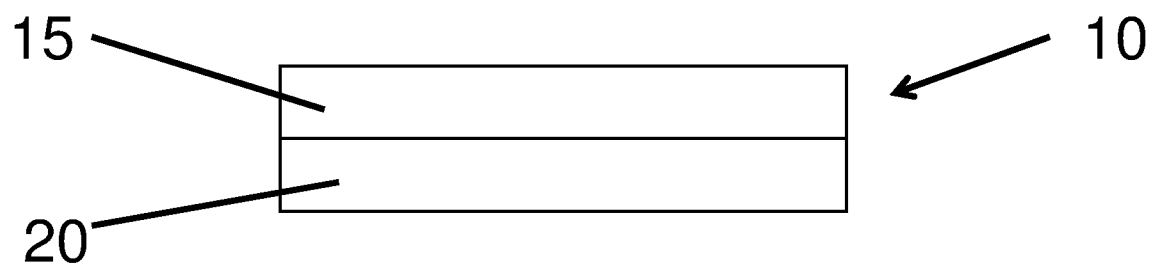
FIG. 1 is a schematic diagram of an example of a display device having filter comprising the compound described herein.

The embodiments herein describe new squarylium compounds. By employing a newly designed molecular structure, an example shown below, we report a new series of squarylium compounds that can be used in display device applications. The term "squarylium" is commonly used to describe compounds prepared from squaric acid (which is also known as quadratic acid and more technically as 3,4-dihydroxycyclobut-3-ene-1,2-dione). The term "squarylium" is interchangeable with the terms squarylium dye, squarain, squaraine, and squaraine dye. The squarylium compounds of following formulae can be compounds which effectively and selectively absorb light in the region 550 to 630 nm, between a green color and a red color, with a particularly narrow half-value width so that they may aid in the distinction between perceived green or red colors. Therefore, they can be particularly useful dyes for color correction, improving color purity or broadening the color reproduction range. In some embodiments, the squarylium compound is described by one of the following chemical formulae:

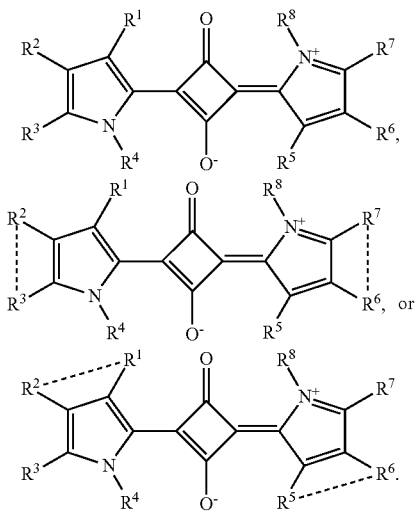

In some embodiments, $R^1$, $R^2$, $R^3$, $R^5$, $R^6$, and $R^7$ are independently H, optionally substituted $C_{1-24}$ hydrocarbyl (including optionally substituted cyclohydrocarbyl, such as optionally substituted $C_{3-10}$ cyclohydrocarbyl) halogen, optionally substituted $C_{1-24}$—S-hydrocarbyl, or optionally substituted $C_{1-24}$—O-hydrocarbyl, and the dashed line represents the presence or absence of a covalent bond. In some embodiments, $R^4$ and $R^8$ are independently H, or optionally substituted $C_{1-24}$ hydrocarbyl (including optionally substituted cyclohydrocarbyl, such as optionally substituted $C_{3-10}$ cyclohydrocarbyl).

In some embodiments, $R^1$, $R^2$ and $R^3$ may be independently be H, optionally substituted $C_{1-24}$ hydrocarbyl (including cyclohydrocarbyl, such as optionally substituted $C_{3-10}$ cyclohydrocarbyl), halogen, optionally substituted —S-hydrocarbyl, or optionally substituted —O-hydrocarbyl. The $C_{1-24}$ hydrocarbyl moiety may be, for example, methyl, ethyl, propyl, butyl, isopropyl, isobutyl, tert-butyl, $C_5$ alkyl, $C_6$ alkyl, $C_7$ alkyl, $C_8$ alkyl, $C_9$ alkyl, $C_{10}$ alkyl, octadecanyl, optionally substituted benzyl, 4-methoxybenzyl, optionally substituted ethylphenyl, optionally substituted phenethyl, 4-bromophenethyl, 2,4-dichlorophenethyl, optionally substituted propylphenyl, optionally substituted ethylnaphthyl, optionally substituted naphthylethyl, etc. The $C_{3-10}$ cyclohydrocarbyl may be, for example, optionally substituted cyclopropyl, cyclobutyl, cyclopentyl, cyclohexyl, cycloheptyl, etc. The halogen may be F, Cl, Br, or I. The —S-hydrocarbyl may be optionally substituted —S-methyl, —S-ethyl, —S-propyl, $C_4$—S-alkyl, $C_5$—S-alkyl, $C_6$—S-alkyl optionally substituted —S-phenyl, optionally substituted —S-benzyl, optionally substituted —S-ethylphenyl, optionally substituted —S-propylphenyl, etc. The —O-hydrocarbyl may be optionally substituted —O-methyl, —O-ethyl, —O-propyl, —O-isopropyl, $C_4$—O-alkyl, $C_5$—O-alkyl, $C_6$—O-alkyl, optionally substituted —O-phenyl, optionally substituted —O-benzyl, optionally substituted —O-ethylphenyl, optionally substituted —O-propylphenyl, etc.

In some embodiments, $R^4$ may be H, optionally substituted $C_{1-24}$ hydrocarbyl (including cyclohydrocarbyl, such as optionally substituted $C_{3-10}$ cyclohydrocarbyl). The $C_{1-24}$ hydrocarbyl moiety may be methyl, ethyl, propyl, butyl, isopropyl, isobutyl, tert-butyl, $C_5$ alkyl, $C_6$ alkyl, $C_7$ alkyl, $C_8$ alkyl, $C_9$ alkyl, $C_{10}$ alkyl octadecanyl, optionally substituted benzyl, 4-methoxybenzyl, optionally substituted methylnaphthyl, optionally substituted ethylphenyl, optionally substituted phenethyl, 4-bromophenethyl, 2,4-dichlorophenethyl, optionally substituted propylphenyl, optionally substituted ethylnaphthyl, optionally substituted naphthylethyl, etc. The $C_{3-10}$ cyclohydrocarbyl may be cyclopropyl, cyclobutyl, cyclopentyl, cyclohexyl, cycloheptyl, etc. In some embodiments, ethylphenyl is —CH$_2$CH$_2$Ph. In some embodiments, the optionally substituted ethylphenyl is —CH$_2$CH$_2$(2,4-dichlorophenyl). In some embodiments, the optionally substituted ethylphenyl is —CH$_2$CH$_2$(4-bromophenyl). In some embodiments, propylphenyl is —CH$_2$CH$_2$CH$_2$Ph. In some embodiments, the optionally substituted methylnaphthyl is —CH$_2$(1-naphthyl). In some embodiments, the optionally substituted methylnaphthyl is —CH$_2$(2-naphthyl). In some embodiments, the optionally substituted ethylnaphthyl is —CH$_2$CH$_2$(1-naphthyl). In some embodiments, the optionally substituted ethylnaphthyl is —CH$_2$CH$_2$(2-naphthyl).

In some embodiments, $R^5$, $R^6$ and $R^7$ may be H, optionally substituted $C_{1-24}$ hydrocarbyl (including cyclohydrocarbyl, such as optionally substituted $C_{3-10}$ cyclohydrocarbyl), halogen, optionally substituted —S-hydrocarbyl, or optionally substituted —O-hydrocarbyl. The $C_{1-24}$ hydrocarbyl moiety may be methyl, ethyl, propyl, butyl, isopropyl, isobutyl, tert-butyl, $C_5$ alkyl, $C_6$ alkyl, $C_7$ alkyl, $C_8$ alkyl, $C_9$ alkyl, $C_{10}$ alkyl octadecanyl, optionally substituted benzyl, 4-methoxybenzyl, optionally substituted ethylphenyl, optionally substituted phenethyl, 4-bromophenethyl, 2,4-dichlorophenethyl, optionally substituted propylphenyl, optionally substituted ethylnaphthyl, optionally substituted naphthylethyl, etc. The $C_{3-10}$ cyclohydrocarbyl may be optionally substituted cyclopropyl, cyclobutyl, cyclopentyl, cyclohexyl, cycloheptyl, etc. The halogen may be F, Cl, Br, or I. The —S-hydrocarbyl may be optionally substituted —S-methyl, —S-ethyl, —S-propyl, $C_4$—S-alkyl, $C_5$—S-alkyl, $C_6$—S-alkyl, optionally substituted —S-phenyl, optionally substituted —S-benzyl, optionally substituted —S-ethylphenyl, optionally substituted —S-propylphenyl, etc. The —O-hydrocarbyl may be optionally substituted —O-methyl, —O-ethyl, —O-propyl, —O-isopropyl, $C_4$—O-alkyl, $C_5$—O-alkyl, $C_6$—O-alkyl, optionally substituted —O-phenyl, optionally substituted —O-benzyl, optionally substituted —O-ethylphenyl, optionally substituted —O-propylphenyl, etc.

In some embodiments, $R^8$ may be H, optionally substituted $C_{1-24}$ hydrocarbyl (including cyclohydrocarbyl, such as optionally substituted $C_{3-10}$ cyclohydrocarbyl). The $C_{1-24}$ hydrocarbyl moiety may be methyl, ethyl, propyl, butyl, isopropyl, isobutyl, tert-butyl, $C_5$ alkyl, $C_6$ alkyl, $C_7$ alkyl, $C_8$ alkyl, $C_9$ alkyl, $C_{10}$ alkyl octadecanyl, optionally substituted benzyl, 4-methoxybenzyl, optionally substituted methylnaphthyl, optionally substituted ethylphenyl, optionally substituted phenethyl, 4-bromophenethyl, 2,4-dichlorophenethyl, optionally substituted propylphenyl, optionally substituted ethylnaphthyl, optionally substituted naphthylethyl, etc. The $C_{3-10}$ cyclohydrocarbyl may be cyclopropyl, cyclobutyl, cyclopentyl, cyclohexyl, cycloheptyl, etc. In some embodiments, ethylphenyl is —CH$_2$CH$_2$Ph. In some embodiments, the optionally substituted ethylphenyl is —CH$_2$CH$_2$(2,4-dichlorophenyl). In some embodiments, the optionally substituted ethylphenyl is —CH$_2$CH$_2$(4-bromophenyl). In some embodiments, propylphenyl is —CH$_2$CH$_2$CH$_2$Ph. In some embodiments, the optionally substituted methylnaphthyl is —CH$_2$(1-naphthyl). In some embodiments, the optionally substituted methylnaphthyl is —CH$_2$(2-naphthyl). In some embodiments, the optionally substituted ethylnaphthyl is —CH$_2$CH$_2$(1-naphthyl). In some embodiments, the optionally substituted ethylnaphthyl is —CH$_2$CH$_2$(2-naphthyl).

In some embodiments, $R^1$ is identical to $R^5$. In some embodiments, $R^2$ is identical to $R^6$. In some embodiments, $R^3$ is identical to $R^7$. In some embodiments, $R^4$ is identical to $R^8$.

In some embodiments, $R^2$ and $R^3$ may form a ring such as shown below:

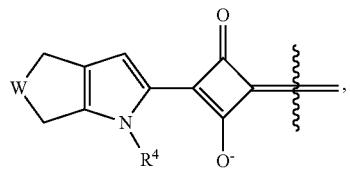

wherein W is $C_nH_{2n}$, wherein n is 0, 1, 2, 3, 4, 5, 6, 7, 8, 9, or 10, and the —CH$_2$—C$_n$H$_{2n}$—CH$_2$— may be optionally substituted. In some embodiments where $C_nH_{2n}$ is —CH$_2$CH$_2$—, this ring structure may be termed a cyclohexapyrrolyl (tetrahydroindolyl) ring, and may be optionally substituted. In some embodiments where $C_nH_{2n}$ is —CH$_2$—, the ring system can be a cyclopentapyrrolyl ring, and may be optionally substituted. In some embodiments where $C_nH_{2n}$ is —CH$_2$CH$_2$CH$_2$—, the ring system can be referred to as a cycloheptapyrrolyl ring, and may be optionally substituted.

In some embodiments, $R^6$ and $R^7$ may form a ring such as shown below:

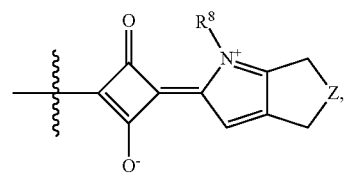

wherein Z is $C_mH_{2m}$, wherein m is 0, 1, 2, 3, 4, 5, 6, 7, 8, 9, or 10, and the —CH$_2$—C$_m$H$_{2m}$—CH$_2$— may be optionally substituted. In some embodiments where $C_mH_{2m}$ is —CH$_2$CH$_2$—, this ring structure may be termed a cyclohexapyrrolyl (tetrahydroindolyl) ring, and may be optionally substituted. In some embodiments where $C_mH_{2m}$ is —CH$_2$—, the ring system can be a cyclopentapyrrolyl ring, and may be optionally substituted. In some embodiments where $C_mH_{2m}$ is —CH$_2$CH$_2$CH$_2$—, the ring system can be a cycloheptapyrrolyl ring, and may be optionally substituted.

In some embodiments, $R^2$ and $R^3$ may form a ring and also $R^6$ and $R^7$ may form a ring structure such as shown below:

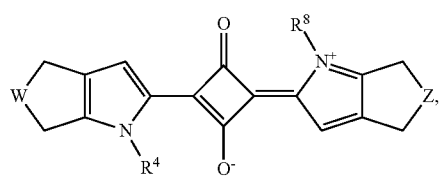

wherein W is $C_nH_{2n}$, wherein n is 0, 1, 2, 3, 4, 5, 6, 7, 8, 9, or 10, and the —CH$_2$—C$_n$H$_{2n}$—CH$_2$— may be optionally substituted; Z is $C_mH_{2m}$, wherein m is 0, 1, 2, 3, 4, 5, 6, 7, 8, 9, or 10, and the —CH$_2$—C$_m$H$_{2m}$—CH$_2$— may be optionally substituted. In some embodiments where $C_nH_{2n}$ is —CH$_2$CH$_2$— and $C_mH_{2m}$ is —CH$_2$CH$_2$—, this ring structure may be termed a cyclohexapyrrolyl (tetrahydroindolyl) ring, which may be optionally substituted. In some embodiments where $C_nH_{2n}$ is —CH$_2$— and $C_mH_{2m}$ is —CH$_2$—, the ring system can be a cyclopentapyrrolyl ring, which may be optionally substituted. In some embodiments where $C_nH_{2n}$ is —CH$_2$CH$_2$CH$_2$— and $C_mH_{2m}$ is —CH$_2$CH$_2$CH$_2$—, the ring system can be a cycloheptapyrrolyl ring, which may be optionally substituted.

In some embodiments, $R^1$ and $R^2$ may form a ring such as shown below:

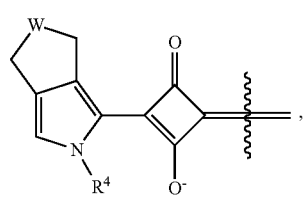

wherein W is $C_nH_{2n}$, wherein n is, 0, 1, 2, 3, 4, 5, 6, 7, 8, 9, or 10, and the —CH$_2$—C$_n$H$_{2n}$—CH$_2$— may be optionally substituted. In some embodiments where $C_nH_{2n}$ is —CH$_2$CH$_2$—, this ring structure may be termed a cyclohexapyrrolyl (tetrahydro-isoindolyl) ring, which may be optionally substituted. In some embodiments where $C_nH_{2n}$ is —CH$_2$—, the ring system can be a cyclopentapyrrolyl ring, which may be optionally substituted. In some embodiments where $C_nH_{2n}$ is —CH$_2$CH$_2$CH$_2$—, the ring system can be a cycloheptapyrrolyl ring, which may be optionally substituted.

In some embodiments, $R^5$ and $R^6$ may form a ring structure such as shown below:

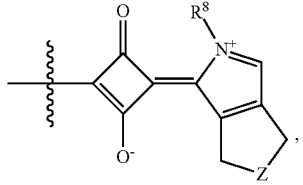

wherein Z is $C_mH_{2m}$, wherein m is 0, 1, 2, 3, 4, 5, 6, 7, 8, 9, or 10, and the —$CH_2$—$C_mH_{2m}$—$CH_2$— may be optionally substituted. In some embodiments where $C_mH_{2m}$ is —$CH_2CH_2$—, this ring structure may be termed a cyclohexapyrrolyl (tetrahydro-isoindolyl) ring, which may be optionally substituted. In some embodiments where $C_mH_{2m}$ is —$CH_2$—, the ring system can be a cyclopentapyrrolyl ring, which may be optionally substituted. In some embodiments where $C_mH_{2m}$ is —$CH_2CH_2CH_2$—, the ring system can be a cycloheptapyrrolyl ring, which may be optionally substituted.

In some embodiments, $R^1$ and $R^2$ may form a ring structure and also $R^5$ and $R^6$ may form a ring structure such as shown below:

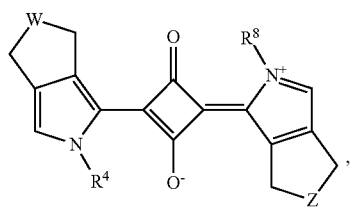

wherein W is $C_nH_{2n}$, wherein n is 0, 1, 2, 3, 4, 5, 6, 7, 8, 9, or 10, and the —$CH_2$—$C_nH_{2n}$—$CH_2$— may be optionally substituted; Z is $C_mH_{2m}$, wherein m is 0, 1, 2, 3, 4, 5, 6, 7, 8, 9, or 10, and the —$CH_2$—$C_mH_{2m}$—$CH_2$— may be optionally substituted. In some embodiments where $C_nH_{2n}$ is —$CH_2CH_2$— and $C_mH_{2m}$ is —$CH_2CH_2$—, this ring structure may be termed a cyclohexapyrrolyl (tetrahydro-isoindolyl) ring, which may be optionally substituted. In some embodiments where $C_nH_{2n}$ is —$CH_2$— and $C_mH_{2m}$ is —$CH_2$—, the ring system can be a cyclopentapyrrolyl ring, which may be optionally substituted. In some embodiments where $C_nH_{2n}$ is —$CH_2CH_2CH_2$— and $C_mH_{2m}$ is —$CH_2CH_2CH_2$—, the ring system can be a cycloheptapyrrolyl ring, which may be optionally substituted.

In some embodiments, the ring formed by the covalent bonding ring structure of $R^2$ and $R^3$ may be optionally substituted such as shown in the following structures:

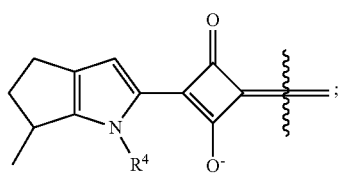

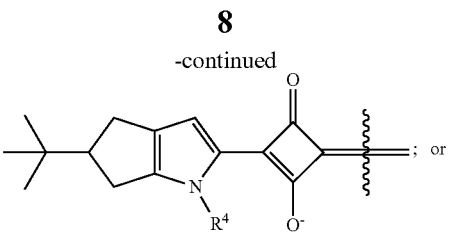

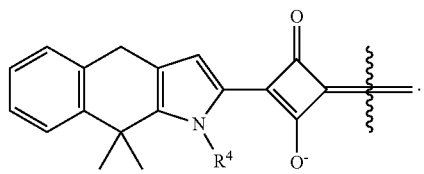

The latter ring structure may be termed a substituted dihydrobenzoindolyl ring.

In some embodiments, the ring formed by the covalent bonding ring structure of $R^6$ and $R^7$ may be optionally substituted such as shown in the following structures:

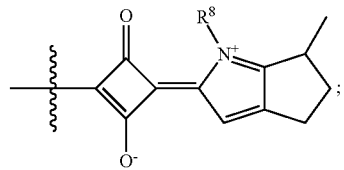

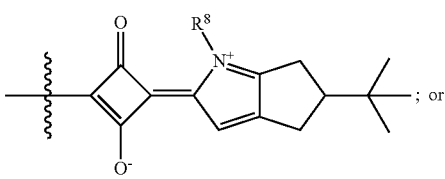

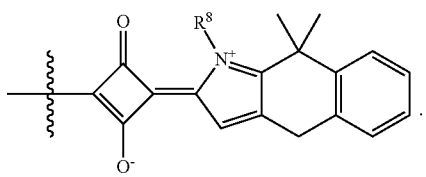

The latter ring structure may be termed a substituted dihydrobenzoindolyl ring.

In some embodiments, the rings formed by the covalent bonding ring structure of $R^2$ with $R^3$ and also $R^6$ with $R^7$ may be optionally substituted as shown in the following structures:

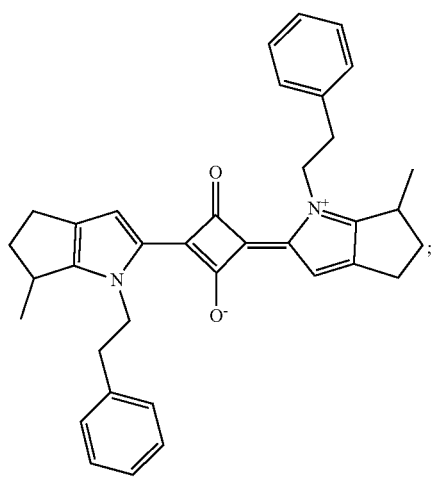

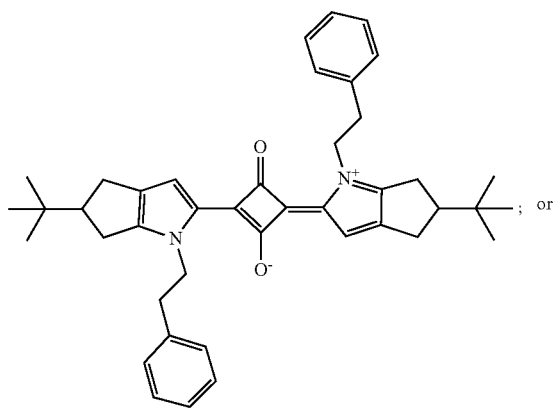; or

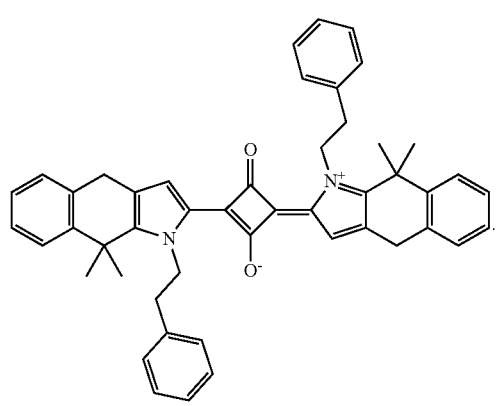.

The latter ring structure may be termed a dihydrobenzoindolyl ring.

In some embodiments, the ring formed by the covalent bonding of $R^1$ and $R^2$ may be optionally substituted. In some embodiments, the ring formed by the covalent bonding of $R^5$ and $R^6$ may be optionally substituted. In some embodiments, the rings formed by the covalent bonding of $R^1$ with $R^2$ and also $R^5$ with $R^6$ may be optionally substituted.

In some embodiments, the squarylium compound is:

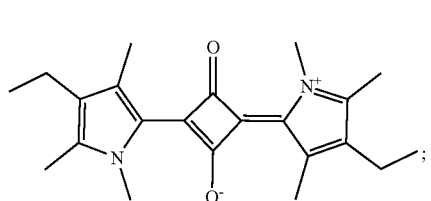

SQL-1

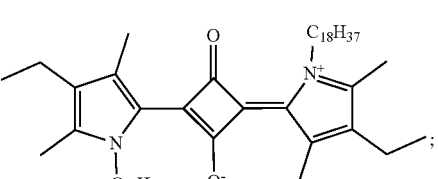

SQL-2

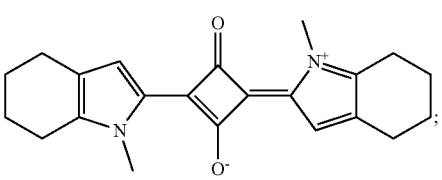

SQL-3

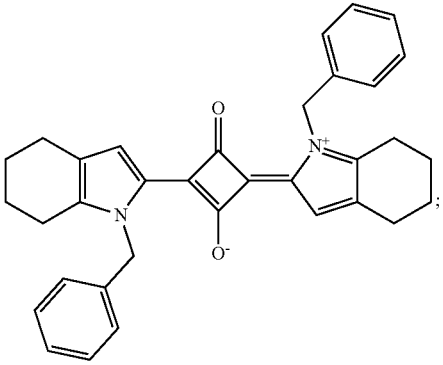

SQL-4

SQL-5

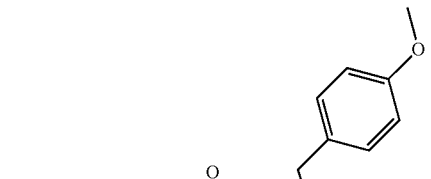

SQL-6

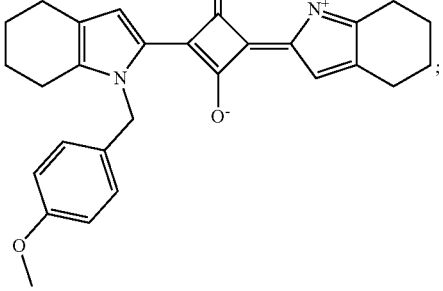

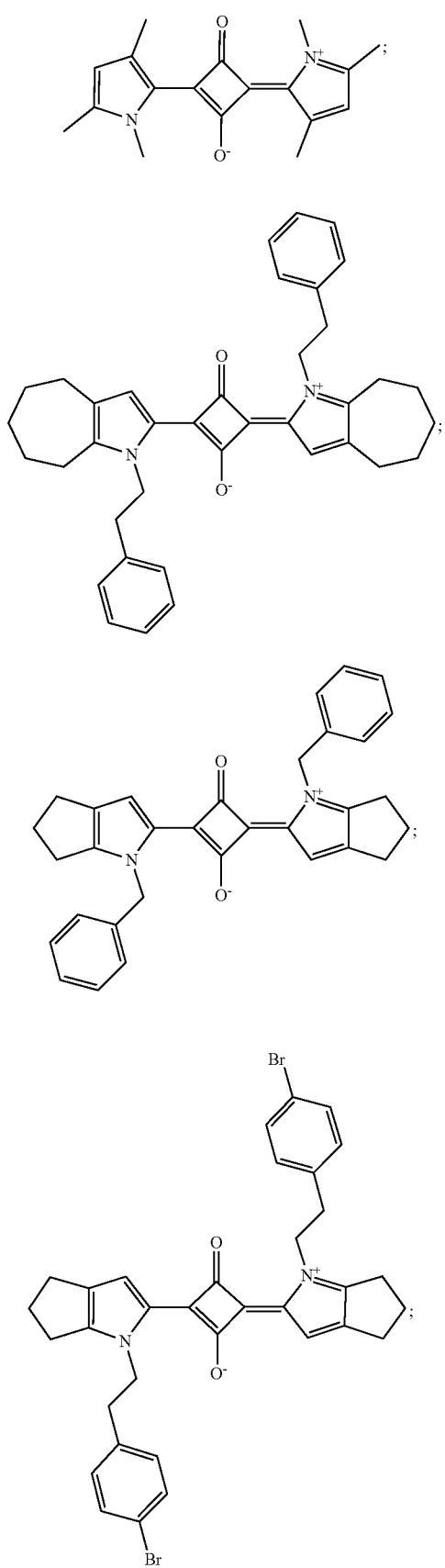
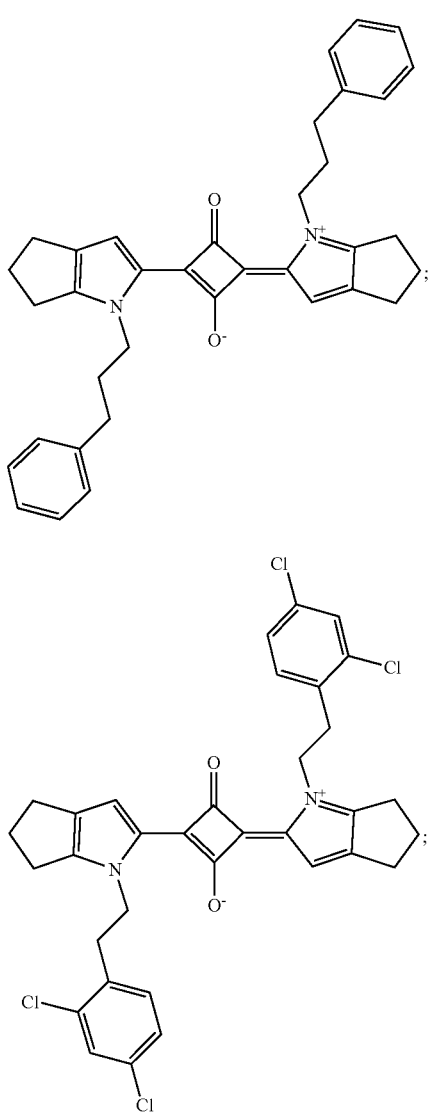

SQL-14
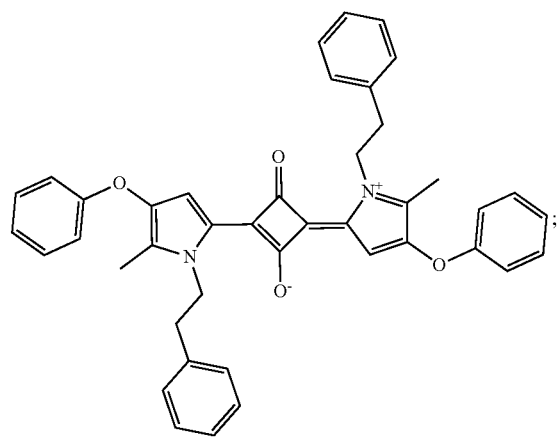
SQL-15
SQL-16
SQL-17
SQL-18
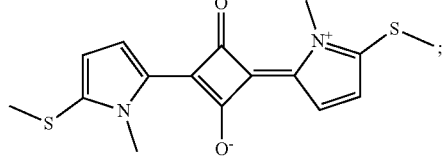
SQL-19
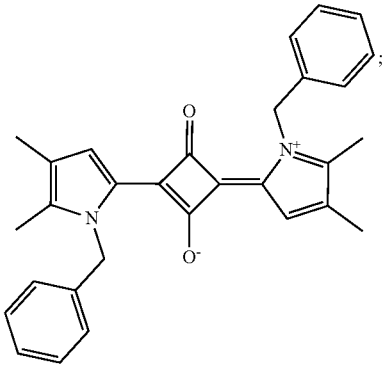
SQL-20
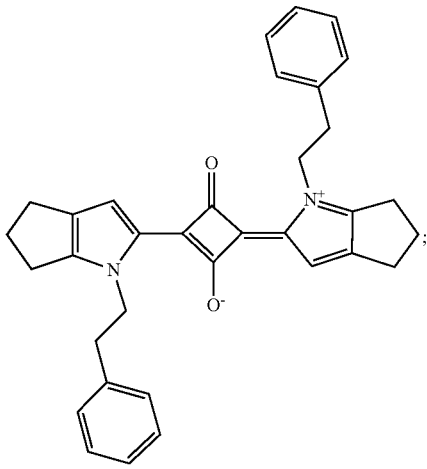
SQL-21
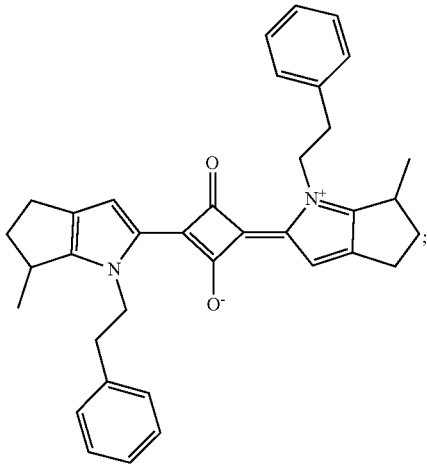

-continued
SQL-22
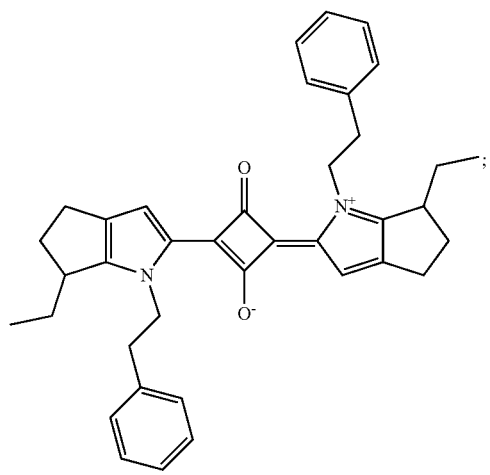
SQL-23
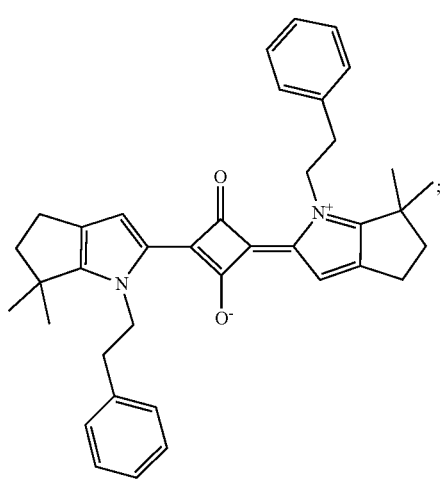
SQL-24
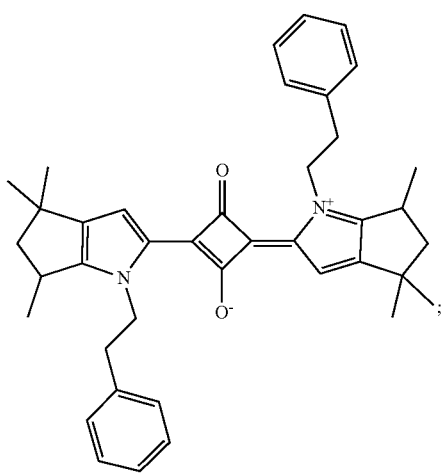
-continued
SQL-25
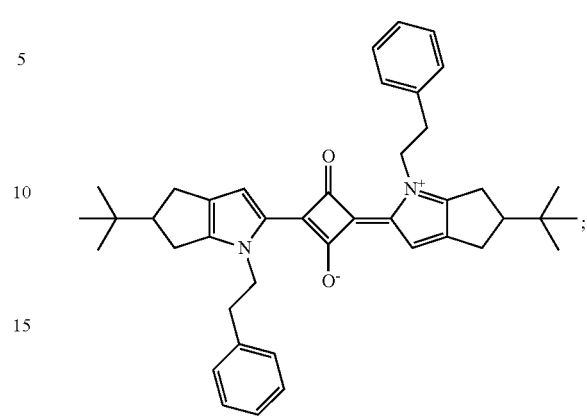
SQL-26
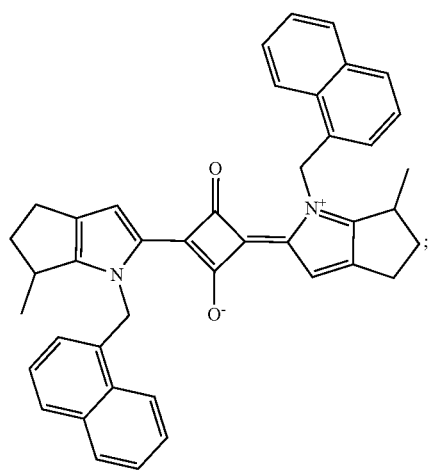
SQL-27
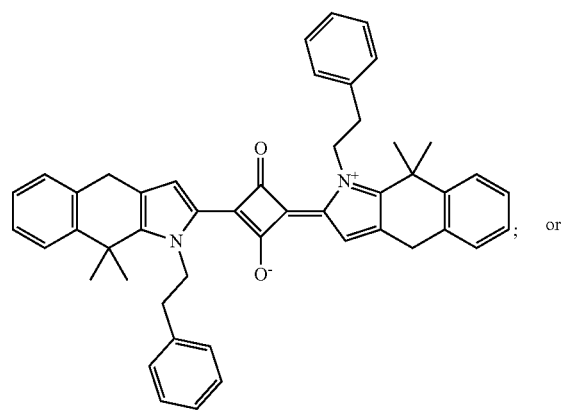 or

SQL-28

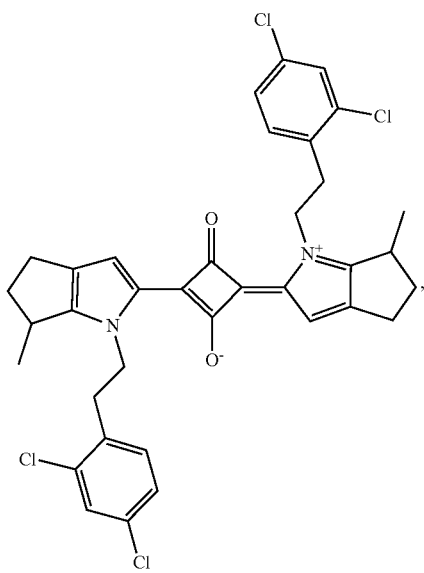

or a combination thereof.

The squarylium compounds described herein effectively and selectively absorb light in the visible light spectrum between about 550-630 nanometers (nm), which is the region between a green color and a red color. In some embodiments, the squarylium compounds have an absorption wavelength between about 560-620 nm. In some embodiments, the squarylium compounds have an absorption wavelength between about 570-580 nm, about 580-590 nm, about 590-600 nm, about 600-610 nm, about 610-620 nm, about 620-630 nm, about 575-615 nm or about 580-610 nm. In some embodiments, the compounds can have an absorption spectra with a reduced, absent or substantially absent shoulder on the 550 nm side of the absorption spectra. In some embodiments, the 550 nm side of the absorption spectra can be a reduced, absent or substantially absent shoulder between 525 to around 550 nm, e.g., about 530 nm. It is believed that reducing the absorption shoulder reduces the overlap with a display devices' green emission.

In some embodiments, the squarylium compounds described herein have a narrow absorption band. The full width at half maximum (FWHM) can be described as the width of an absorption or emission band in nm at the absorption or emission band intensity that is half the maximum of the absorption or emission value for the band. In some embodiments, the squarylium compounds described herein have, when dispersed in substantially transparent matrix, a FWHM is less than or equal to about 50 nm, about 45-50 nm, about 40-45 nm, about 35-40 nm, about 30-35 nm, about 27-30 nm, about 25-27 nm, less than or equal to 40 nm, or less than or equal to about 25 nm.

The fluorescence quantum yield gives the efficiency of the fluorescence process, e.g. the ratio of the number of photons emitted to the number of photons absorbed, Φ. Fluorescence quantum yield may be has high as 1.0 (100%), where each photon absorbed results in a photon emitted. Compounds with quantum yields of 0.10 are still considered quite fluorescent. Quantum yield measurements can be made by comparing the integrated fluorescence emission of the squarylium compound described herein with the integrated fluorescence of nile blue A (QY=0.23 in ethanol) at equal dye absorbance, at the excitation wavelength. The fluorescence of buffer alone is subtracted from that of the sample for each measurement. In some embodiments, the squarylium compounds can be weakly fluorescent or essentially non-fluorescent. In some embodiments, the squarylium compounds described herein can have a low quantum yield. In some embodiments the quantum yield can be less than about 0.1 (10%). In some embodiments, the fluorescence quantum yield can be less than or equal to about 0.020 (2%), about 0.010 (1%), about 0.0075 (0.75%), about 0.0065 (0.65%), about 0.0050 (0.50%), about 0.0045 (0.45%), about 0.0040 (0.40%), or about 0.0030 (0.30%).

Some embodiments include a filter comprising a compound described above. In some embodiments, the filter can additionally comprise a non-squarylium compound. In some embodiments, the non-squarylium compound can be a second dye. In some embodiments, the mixture of the squarylium dye and the non-squarylium dye can display reduced shoulders on the 550 nm side of the absorption spectra. In some embodiments, the squarylium and the non-squarylium dye can have concurrent absorption maximum within the absorbance maximum wavelength ranges described above. In some embodiments, a display device can comprise the compound as described above. The filter for a display according to the invention contains at least one dye selected from the squarylium compounds of formulae described herein. Representative examples of the configuration of the filter includes a laminate structure composed of a transparent sheet or film substrate and a resin layer containing the squarylium compound and a binder resin, and/or a single layer structure, i.e., a sheet or film made of a resin containing the squarylium compound.

In using two or more squarylium compounds, they can be mixed together into a single layer of the above laminate or a single film above, or a plurality of layers or films each containing a squarylium compound may be provided. In such a case, a laminate is formed even in the above-described latter case. Moreover, by changing the binder resins depending on the respective squarylium compounds used, a subtle toning can be obtained.

The former laminate filter can be prepared by, for example, (1) a method comprising dissolving or dispersing the squarylium compound and a binder resin in an appropriate solvent and applying the solution or dispersion on a transparent sheet or film substrate by a conventional method, followed by drying, (2) a method comprising melt-kneading the squarylium compound and a binder resin, molding the mixture into a film or a sheet by a conventional molding technique for thermoplastic resins such as extrusion, injection molding or compression molding, and adhering the film or sheet to a transparent substrate, e.g., with an adhesive, (3) a method comprising extrusion laminating a molten mixture of the squarylium compound and a binder resin on a transparent substrate, (4) a method comprising co-extruding a molten mixture of the squarylium compound and a binder resin with a molten resin for a transparent substrate, or (5) a method comprising molding a binder resin into a film or a sheet by extrusion, injection molding, compression molding, etc., bringing the film or the sheet into contact with a solution of the squarylium compound, and the thus dyed film or sheet is adhered to a transparent substrate, e.g., with an adhesive.

The latter single layer sheet or film comprising a resin containing the squarylium compound is prepared by, for example, (6) a method comprising casting a solution or dispersion of the squarylium compound and a binder resin in an appropriate solvent on a carrier followed by drying, (7) a method comprising melt-kneading the squarylium compound and a binder resin and molding the mixture into a film or a sheet by a conventional molding technique for thermoplastic resins such as extrusion, injection molding or compression molding, or (8) a method comprising molding a binder resin into a film or a sheet by extrusion, injection molding, compression molding, etc. and bringing the film or the sheet into contact with a solution of the squarylium compound.

For some applications, the laminate filter is preferred to the single layer filter. In some embodiments, the laminate filter may preferably be a laminated filter comprising a transparent substrate formed thereon a squarylium compound-containing resin layer comprising a binder resin containing the squarylium compound, which is produced by coating a transparent sheet or film substrate with a coating composition prepared by dissolving the squarylium compound and a binder resin in an appropriate solvent or dispersing the particles of the squarylium compound having a particle size of 0.1 to 3 micrometers and a binder resin in a solvent and drying the coating film.

The method of making the filter may be chosen according to the layer structure and material fit for a particular use. Taking for instance a filter for display devices, e.g., liquid crystal display (LCD) and/or plasma display panels (PDPs), which is an embodiment of the present invention, the following production method is preferred.

Materials of the transparent substrate which can be used in the filter for displays are not particularly limited as far as they are substantially transparent, having little light absorption and causing little light scattering, e.g. having a transmittance that is at least 50%, at least 70%, at least 80%, at least 90%, at least 95%, or at least 99%. Examples of suitable materials include glass, polyolefin resins, amorphous polyolefin resins, polyester resins, polycarbonate resins, acrylic resins, polystyrene resins, polyvinyl chloride resins, polyvinyl acetate resins, polyarylate resins, and polyether sulfone resins. Examples of these suitable materials can be amorphous polyolefin resins, polyester resins, polycarbonate resins, acrylic resins, polyarylate resins, and/or polyether sulfone resins.

The resin can be molded into a film or a sheet by conventional molding methods, such as injection molding, T-die extrusion, calendering and compression molding, and/or by casting a solution of the resin in an organic solvent. The resin can contain commonly known additives, such as anti-heat aging agents, lubricants, and antioxidants. The substrate can have a thickness of 10 micrometers to 5 mm. The resin film or sheet may be unstretched or stretched film or sheet. The substrate may be a laminate of the above-described material and other films or sheets.

If desired, the transparent substrate can be subjected to a known surface treatment, such as a corona discharge treatment, a flame treatment, a plasma treatment, a glow discharge treatment, a surface roughening treatment, and a chemical treatment. If desired, the substrate can be coated with an anchoring agent or a primer.

The binder resin which can be used with the squarylium compound(s) includes resins such as acrylic resins, polycarbonate resins, ethylene-vinyl alcohol copolymer resins, ethylene-vinyl acetate copolymer resins and saponification products thereof, AS resins, polyester resins, vinyl chloride-vinyl acetate copolymer resins, polyvinyl butyral resins, polyvinylphosphonic acid (PVPA), polystyrene resins, phenolic resins, phenoxy resins, polysulfone, nylon, cellulosic resins, and cellulose acetate resins. In some embodiments, the binder resin can be a polyester resin and/or acrylic resin.

The solvent which can be used for dissolving or dispersing the dye and the resin can include an alkane, such as butane, pentane, hexane, heptane, and octane; cycloalkanes, such as cyclopentane, cyclohexane, cycloheptane, and cyclooctane; alcohols, such as ethanol, propanol, butanol, amyl alcohol, hexanol, heptanol, octanol, decanol, undecanol, diacetone alcohol, and furfuryl alcohol; cellosolves, such as methyl cellosolve, ethyl cellosolve, butyl cellosolve, methyl cellosolve acetate, and ethyl cellosolve acetate; propylene glycol and its derivatives, such as propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate, and dipropylene glycol dimethyl ether; ketones, such as acetone, methyl amyl ketone, cyclohexanone, and acetophenone; ethers, such as dioxane and tetrahydrofuran; esters, such as butyl acetate, amyl acetate, ethyl butyrate, butyl butyrate, diethyl oxalate, ethyl pyruvate, ethyl 2-hydroxybutyrate, ethyl acetoacetate, methyl lactate, ethyl lactate, and methyl 3-methoxypropionate; halogenated hydrocarbons, such as chloroform, methylene chloride, and tetrachloroethane; aromatic hydrocarbons, such as benzene, toluene, xylene, and cresol; and highly polar solvents, such as dimethyl formamide, dimethyl acetamide, and N-methylpyrrolidone.

An RGB source is a light source which emits at the same time red, green and blue light. Such sources are often used for color display applications. A wide range of colors can be obtained by mixing different amounts of red, green and blue light (additive color mixing). Suitable RGB sources include, but are not limited to a cathode ray tube (CRT), liquid crystal display (LCD), plasma display, or organic light emitting diode (OLED) display such as a television, a computer's monitor, or a large scale screen. Each pixel on the screen can be built by driving three small and very close but still separated RGB light sources. At common viewing distance, the separate sources may seem indistinguishable, which can trick the eye to see a given solid color. All the pixels together arranged in the rectangular screen surface conforms the color image.

An example of a configuration of the device comprising a compound described herein is shown in FIG. 1. The device 10 can comprise the following layers in the order given: a filter layer 15 and a display layer 20. In some embodiments, the display layer can be the outermost layer or surface of a display device, e.g., an RGB source. Suitable RGB sources can be a liquid crystal display device, a plasma display panel and/or a cathode ray terminal. In some embodiments, the filter layer 15 can be positioned such that the display layer/RGB source can be viewed therethrough by the viewer. In some embodiments, viewing the RGB source through the filter layer can increase the color distinction between the red and green colors.

EXAMPLES

The following are examples of methods that may be used to prepare and use the compounds described herein.

Example 1.1 (Synthesis of SQL-1)

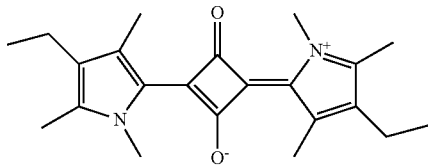

SQL-1

Pulverized 1.20 g potassium hydroxide with a mortar and pestle, charged it into a reactor, and established an argon atmosphere. Added 10 mL DMSO and stirred for 5 minutes. Added 616 mg 3-ethyl-2,4-dimethyl pyrrole then stirred for 50 minutes. Cooled with an ice bath and added 1.42 g of methyl iodide dropwise over 2 minutes. Removed cooling and stirred for 50 minutes. Added 10 mL water then extracted with 20 mL hexanes. Washed the extract with two 20 mL portions of water. Dried with sodium sulfate and concentrated in vacuo to 600 mg of yellow oil. Dissolved 204 mg of the oil in 3 mL ethanol and added it into a vial previously charged with 84 mg squaric acid. Stirred and heated in an 88° C. block heater until boiling, then capped the vial and stirred for 1.5 hours. Cooled to room temperature and filtered the slurry then washed the filter cake with two 1 mL portions of ethanol. Dried at 70° C. in vacuo to 134 mg grey-blue solid product. 1H NMR(CDCl3) 1.06 (t, 3H), 2.28 (s, 3H), 2.40 (q, 2H), 2.62 (s, 3H), 4.03 (s, 3H). MS (APCI, positive mode) 353. Film optical data (Amorphous polycarbonate film): λ max=596 nm, FWHM (Full Width at Half-Maxima)=34 nm.

Example 1.2 (Synthesis of SQL-2)

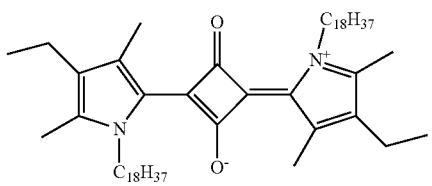

SQL-2

This compound was made in a manner similar to a published procedure: J. Chem. Soc., Perkin Trans. 2, 1998, 779. Film optical data (Amorphous polycarbonate [APC] film): λ max=595 nm, FWHM=35 nm.

Example 1.3 (Synthesis of SQL-3)

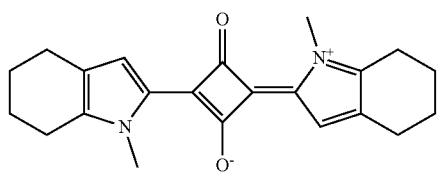

SQL-3

Pulverized 740 mg of potassium hydroxide, placed it into a reactor, and established an argon atmosphere. Added 400 mg 4,5,6,7-tetrahydroindole in 6 mL of DMSO and stirred for 50 minutes. Added 0.41 mL methyl iodide and stirred for 2 h. Added 20 mL water, extracted with 30 mL hexane, and washed the extract twice with 20 mL portions of water. Dried the extract with sodium sulfate and concentrated in vacuo to 380 mg of oil. Dissolved the oil in 5 mL ethanol and poured the resulting solution onto 156 mg of squaric acid in a vial. Stirred and heated the contents of the vial in an 85° C.-block until boiling then capped the vial and stirred for 1 hour and 15 minutes. Cooled to room temperature and filtered, washing the filter cake twice with 2 mL portions of ethanol. Dried the filter cake in vacuo at 70° C. to 315 mg of purple powder product. $^1$H NMR (400 MHz, CDCl3) δ 7.53 (s, 1H), 4.11 (s, 3H), 2.70 (t, J=6.3 Hz, 2H), 2.60 (t, J=6.2 Hz, 2H), 1.90 (ddt, J=12.2, 8.6, 4.7 Hz, 2H), 1.81-1.71 (m, 2H). MS (APCI, positive mode) 349. Film optical data (Amorphous polycarbonate [APC] film): λ max=582 nm, FWHM=26 nm.

Example 1.4 (Synthesis of SQL-4)

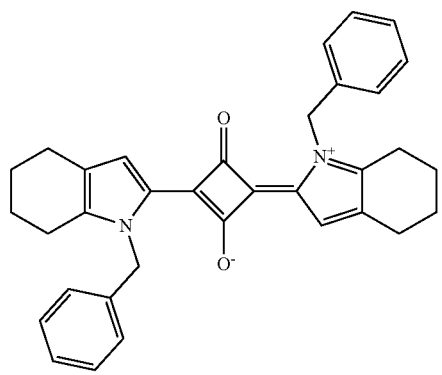

SQL-4

Loaded 335 mg of pulverized potassium hydroxide into a reactor under an argon atmosphere. Added 3 mL dimethylsulfoxide, stirred, and added 181 mg 4,5,6,7-tetrahydroindole. Stirred for 45 minutes, cooled in an icebath, and dripped in 256 mg benzyl bromide. Removed cooling, stirred for 1 hour, diluted with icewater, and extracted with hexanes. Washed the extracts with water, dried them with brine then sodium sulfate, and concentrated to 430 mg of orange oil pyrrole that was used without further purification. Dissolved this in 5 mL ethanol, combined in a vial along with 83 mg squaric acid, sealed the vial, and stirred and heated the contents at 80° C. for 2 hours. Cooled the slurry, filtered it, and washed the filter cake with ethanol. Dried the filter cake at 70° C. under vacuum for 2 hours to 130 mg of squaraine product. $^1$H NMR (400 MHz, Chloroform-d) δ 7.60 (s, 1H), 7.23 (q, J=9.0, 7.4 Hz, 3H), 7.02 (d, J=7.5 Hz, 2H), 5.94 (d, J=14.8 Hz, 2H), 2.60 (q, J=7.0, 6.0 Hz, 2H), 2.53 (t, J=6.3 Hz, 2H), 1.79 (p, J=6.3, 5.8 Hz, 2H), 1.71 (q, J=5.5, 4.9 Hz, 2H). LC-MS (APCI, +) 501. Amorphous polycarbonate film: λ max=585 nm, FWHM=26 nm.

Example 1.5 (Synthesis of SQL-5)

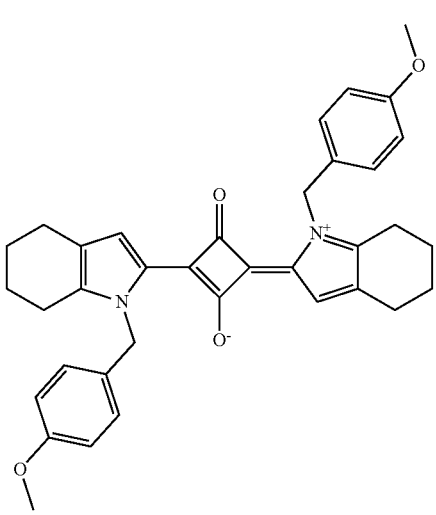

SQL-5

Under argon, 110 mg 4,5,6,7-tetrahydroindole was combined with 220 mg of pulverized potassium hydroxide and 2 mL dimethyl sulfoxide and stirred for 1 hour. 142 mg 4-methoxybenzyl chloride was added and the resulting solution stirred for 45 minutes. 4 mL cool water was added and hexanes was used to extract the resulting solution. The extract was washed with water, dried with sodium sulfate, and concentrated to 160 mg of crude pyrrole. This was dissolved in 2 mL ethanol, added to 30 mg squaric acid, stirred, and heated in a sealed vial at 80° C. for 2 hours. The solution was cooled to room temperature and filtered. The filter cake was dried to 13 mg of product squaraine. $^1$H NMR (400 MHz, Chloroform-d) δ 7.59 (s, 1H), 6.98 (d, J=8.1 Hz, 2H), 6.81 (d, J=8.0 Hz, 2H), 5.86 (s, 2H), 3.77 (s, 3H), 2.57 (dt, J=12.2, 6.1 Hz, 2H), 1.86-1.63 (m, 6H). $^{13}$C NMR (101 MHz, Chloroform-d) δ 158.72, 129.94, 128.27, 126.73, 114.09, 55.23, 49.70, 23.48, 23.01, 22.62, 22.26. HPLC-MS (APCI, +) 561. Amorphous polycarbonate film: λ max=585 nm, FWHM=27 nm.

Example 1.6 (Synthesis of SQL-6)

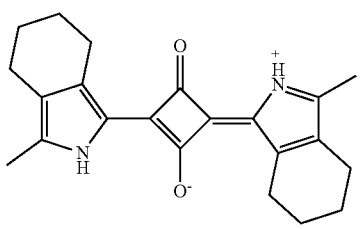

SQL-6

400 mg 4,5,6,7-Tetrahydro-1-methyl-2H-isoindole was synthesized as described in the literature (Kancharla, P et. al., J. Med. Chem., 58(18), 7286-7309; 2015). This was dissolved in 5 mL ethanol, combined with 165 mg squaric acid, and heated in a sealed vial at 80° C. for 2 hours. The slurry was cooled to room temperature and filtered. The filter cake washed with ethanol and dried at 60° C. under vacuum to give 318 mg. LC-MS (APCI, -) 347. Amorphous polycarbonate film: λ max=575 nm, FWHM=26 nm.

Example 1.7 (Synthesis of SQL-7)

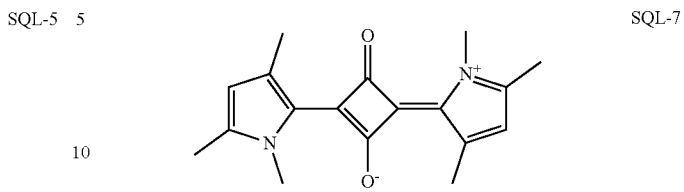

SQL-7

252 mg 2,4-dimethylpyrrole, 630 mg pulverized potassium hydroxide, and 4 mL dimethylsulfoxide were combined in a closed vial and stirred for 45 minutes. Cooled in an icebath and added 1.00 g iodomethane. After 1 hour, added 10 mL water, extracted with hexane, and washed the extract a few times with water. Dried the extracts with sodium sulfate and concentrated to 210 mg yellow oil. This was dissolved in 3 mL ethanol and added onto 105 mg squaric acid in a capped vial. The vial was closed and heated at 80° C. for 2 hours, then cooled to room temperature and filtered. The filter cake was washed with ethanol and dried under vacuum at 70° C. to give 76 mg of product. $^1$H NMR (400 MHz, Chloroform-d) δ 6.10 (s, 1H), 4.04 (s, 3H), 2.67 (s, 3H), 2.32 (s, 3H). $^{13}$C NMR (101 MHz, Chloroform-d) δ 176.79, 175.52, 147.08, 138.84, 127.96, 117.38, 34.57, 15.05, 13.50. LC-MS (APCI, -) 295. Amorphous polycarbonate film: λ max=585 nm, FWHM=40 nm.

Example 1.8 (Synthesis of SQL-8)

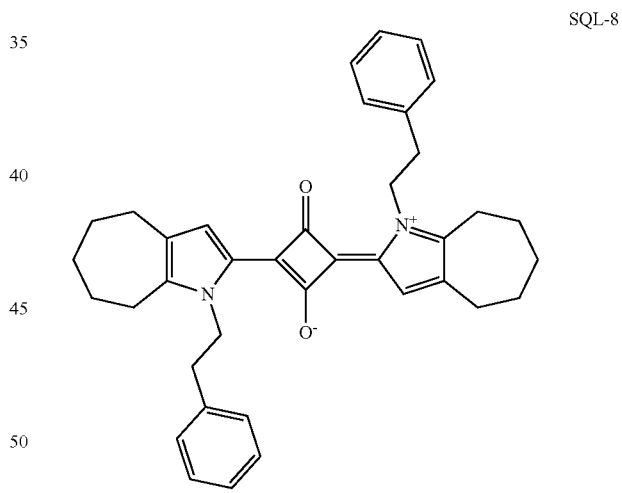

SQL-8

790 mg phenethylamine was dissolved in 5 mL 3-methyl-3-pentanol and added into a reactor containing 664 mg cycloheptanone and 5 mL 3-methyl-3-pentanol. An argon atmosphere was established and the solution heated to 80° C. for 40 minutes. 73 mg dichloro(p-cymene)ruthenium (II) dimer, 138 mg XantPhos, and 0.73 mL ethylene glycol were added and the solution heated in a 125° C.-oil bath for 20 hours. The solvent was removed on a rotary evaporator and the residue purified by silica gel chromatography with an ethyl acetate-hexane gradient. The pyrrole product—446 mg of oil—was contaminated with an impurity, but was used without further purification. 4 mL ethanol was used to dissolve it and this was combined with 106 mg squaric acid in a vial. The vial was sealed and heated at 80° C. for 2 hours. The solution was cooled, filtered, and the filter cake product washed with ethanol. The solid was dried under vacuum at 70° C. to 370 mg of product squaraine. $^1$H NMR (400 MHz, Chloroform-d) δ 7.60 (s, 1H), 7.25 (dt, J=12.3, 7.2 Hz, 3H), 7.14 (d, J=7.3 Hz, 2H), 4.92 (t, J=7.0 Hz, 2H), 3.03 (t, J=7.0 Hz, 2H), 2.63-2.56 (m, 2H), 2.42 (s, 2H), 1.76 (p, J=5.3 Hz, 2H), 1.62 (q, J=5.4 Hz, 2H), 1.45 (s, 2H). $^{13}$C NMR (101 MHz, Chloroform-d) δ 151.41, 138.36, 131.56, 129.28, 128.47, 126.64, 125.91, 48.12, 38.86, 31.83, 28.28, 28.25, 27.17, 26.47. HPLC-MS (APCI, +) 557. Amorphous polycarbonate film: λ max=587 nm, FWHM=25 nm.

Example 1.9 (Synthesis of SQL-9)

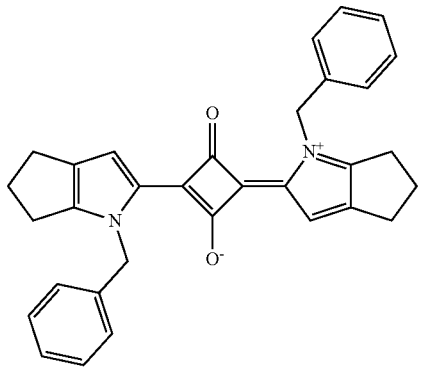

70 mg 1,4,5,6-tetrahydro-1-(phenylmethyl)cyclopenta[b]pyrrole was synthesized as described in the literature (Azzuz, A. et. al. Khimiya Geterotsiklicheskikh Soedinenii, (1), 37-9; 1992). This was dissolved with 1 mL ethanol, combined with 21 mg squaric acid, and heated in a sealed vial at 80° C. for 2 hours. The slurry was cooled, filtered, washed with ethanol, and dried under vacuum at 70° C. to 14 mg of squaraine product. $^1$H NMR (400 MHz, Chloroform-d) δ 7.50 (s, 1H), 7.34-7.23 (m, 2H), 7.16 (d, J=7.3 Hz, 2H), 5.93 (s, 2H), 2.68 (t, J=7.2 Hz, 2H), 2.62 (t, J=7.2 Hz, 2H), 2.41 (dt, J=8.9, 6.4 Hz, 2H). $^{13}$C NMR (101 MHz, Chloroform-d) δ 158.82, 137.57, 135.58, 133.11, 128.72, 127.50, 127.24, 52.55, 28.82, 25.61, 24.82. LC-MS (APCI, +) 473. Amorphous polycarbonate film: λ max 588 nm, FWHM=25 nm.

Example 1.10 (Synthesis of SQL-10)

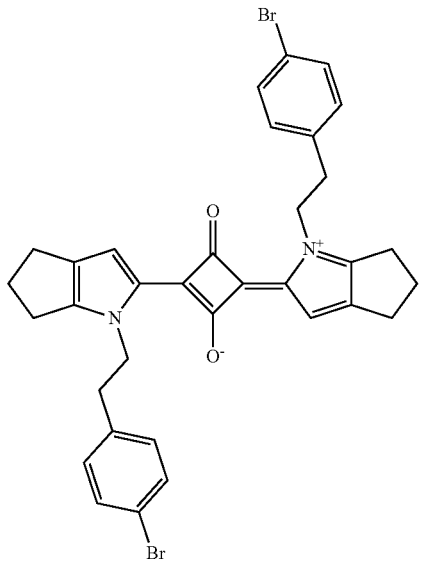

680 mg 4-bromophenethylamine in 4.5 mL of 1-methylcyclohexanol was added to 260 mg of cyclopentanone and 4.5 mL 1-methylcyclohexanol in an argon-filled reactor. The resulting solution was stirred and heated in an 80° C.-oil bath for 30 minutes. 36 mg dichloro(p-cymene)ruthenium (II) dimer, 76 mg XantPhos, and 0.38 mL ethylene glycol was added and the temperature of the oil bath increased to 145° C. After 4.4 hours, cooled and concentrated on rotary evaporator. Purified using silica gel chromatography and ethyl acetate-hexane gradient to give 219 mg of a mixture of pyrrole and an impurity. This material was dissolved in 2 mL ethanol, added onto 43 mg squaric acid, and heated for 2 hours, sealed, at 80° C. The solution was cooled, filtered, the filter cake washed with ethanol and dried under vacuum at 70° C. to give 160 mg of the product squaraine. $^1$H NMR (400 MHz, Chloroform-d) δ 7.50 (s, 1H), 7.42-7.34 (m, 2H), 7.02-6.92 (m, 2H), 4.76 (t, J=6.7 Hz, 2H), 3.06 (t, J=6.6 Hz, 2H), 2.64 (t, J=6.9 Hz, 2H), 2.28 (dq, J=7.8, 6.2 Hz, 2H), 2.21 (d, J=7.1 Hz, 2H). $^{13}$C NMR (101 MHz, Chloroform-d) δ 159.06, 137.61, 134.47, 131.48, 131.33, 131.07, 120.65, 50.41, 38.10, 28.89, 25.02, 24.86. LC-MS (APCI, +) 659. Polymethylmethacrylate film: λ max=588 nm, FWHM=25 nm.

Example 1.11 (Synthesis of SQL-11)

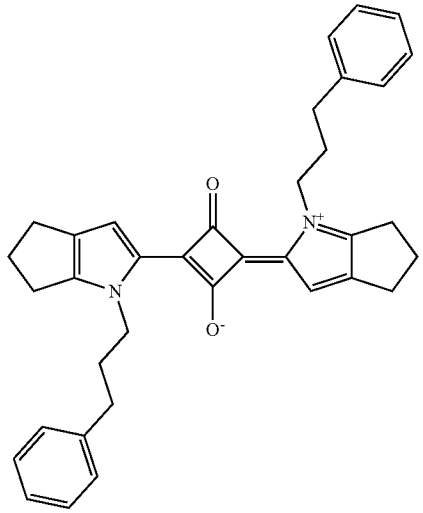

Under argon, a reactor was loaded with 113 mg potassium t-butoxide, 37 mg dichloro(p-cymene)ruthenium (II) dimer, and 69 mg XantPhos. 1.26 mL 3-phenylpropylamine, 0.73 mL ethylene glycol, and 0.52 mL cyclopentanone were successively added into 12 mL 2-methyl-2-butanol and this solution added to the reactor. Heated the reactor in 135° C.-oil for 19 hours, cooled, concentrated on rotary evaporator, and purified with silica gel chromatography using an ethyl acetate-hexanes gradient to give 72 mg of pyrrole. This was dissolved in 1 mL ethanol, added onto 18 mg squaric acid in a vial, sealed the vial, and heated at 80° C. for 2 hours. Cooled, filtered, washed the filter cake with ethanol, and dried the filter cake at 70° C. under vacuum to give 39 mg of squaraine product. $^1$H NMR (400 MHz, Chloroform-d) δ 7.48 (s, 1H), 7.25 (d, J=7.4 Hz, 2H), 7.22-7.13 (m, 3H), 4.67 (t, J=7.2 Hz, 2H), 2.78-2.66 (m, 6H), 2.46 (h, J=7.3, 6.7 Hz, 2H), 2.13 (tt, J=7.8, 6.1 Hz, 2H). $^{13}$C NMR (101 MHz, Chloroform-d) δ 170.23, 158.00, 141.36, 134.76, 132.27, 128.36, 128.33, 125.91, 48.24, 33.44, 32.68, 28.87, 25.33, 24.86. LC-MS (APCI, −) 528. Amorphous polycarbonate film: λ max=588 nm, FWHM=25 nm.

Example 1.12 (Synthesis of SQL-12)

Example 1.13 (Synthesis of SQL-13)

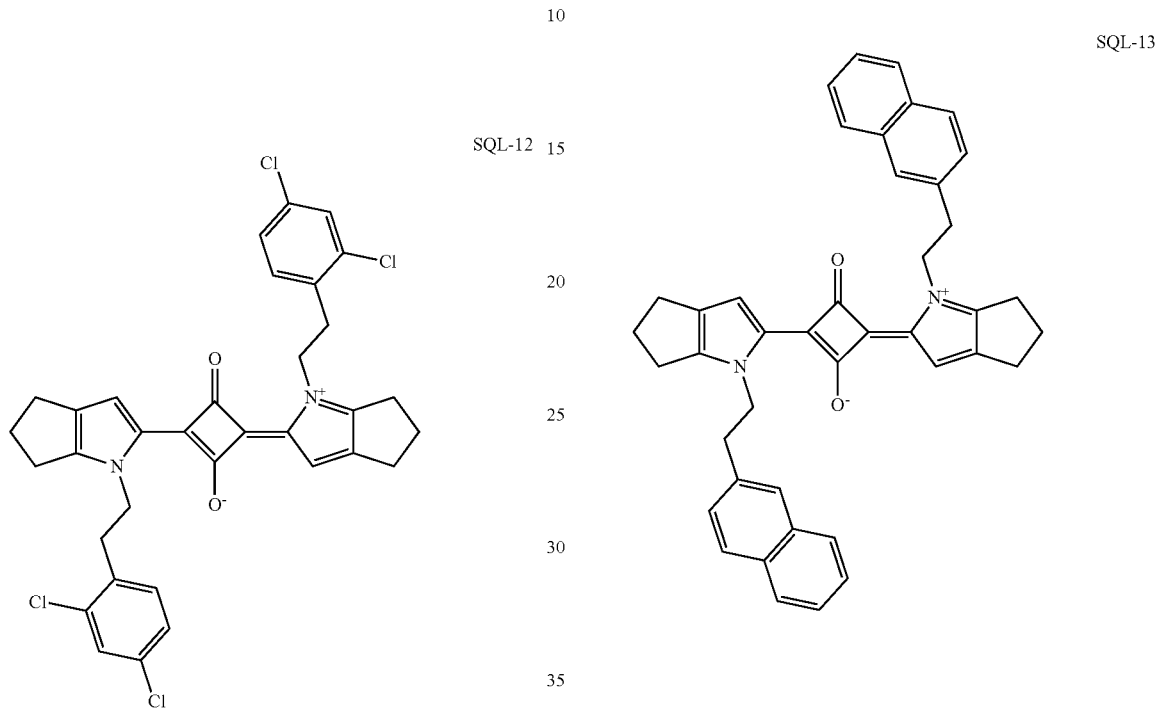

Prepared a reactor containing 260 mg cyclopentanone and 4.5 mL 1-methylcyclohexanol under argon. Added 646 mg 2,4-dichlorophenethylamine dissolved in 4.5 mL 1-methylcyclohexanol and heated the resulting solution in an 80° C.-oil bath for 50 minutes. Added 36 mg dichloro(p-cymene)ruthenium (II) dimer, 76 mg XantPhos, and 0.38 mL ethylene glycol, then heated the oil bath to 145° C. for 3 hours. Cooled, concentrated free of 1-methylcyclohexanol on rotary evaporator, and purified the residue with silica gel-chromatography using an ethyl acetate-hexane gradient. The 187 mg of pyrrole product contained an impurity but was used without further purification. Dissolved it in 2 mL ethanol, added it onto 38 mg squaric acid in a vial, sealed the vial, stirred, and heated at 80° C. for 2 hours. Cooled, filtered, washed the filter cake with ethanol, and dried under vacuum at 70° C. to 163 mg of squaraine product. $^1$H NMR (400 MHz, Chloroform-d) δ 7.50 (s, 1H), 7.40 (d, J=1.9 Hz, 1H), 7.13 (s, 2H), 4.78 (t, J=6.9 Hz, 2H), 3.24 (t, J=6.9 Hz, 2H), 2.64 (t, J=6.8 Hz, 2H), 2.41-2.33 (m, 2H), 2.37-2.25 (m, 2H). $^{13}$C NMR (101 MHz, Chloroform-d) δ 159.03, 134.72, 134.65, 134.62, 133.36, 132.76, 131.45, 129.04, 127.25, 48.23, 35.66, 28.91, 24.98, 24.89. LC-MS (APCI, +) 639. Polymethylmethacrylate film: λ max=589 nm, FWHM=24 nm.

A reactor containing 0.34 g cyclopentanone and 4.5 mL 3-methyl-3-pentanol was prepared and an argon atmosphere established. To this was added a solution of 0.68 g 2-naphthaleneethylamine in 4.5 mL 3-methyl-3-pentanol and the reaction heated in 70° C.-oil for 1 hour. Added 24 mg dichloro(p-cymene)ruthenium (II) dimer, 45 mg XantPhos, and 0.48 mL ethylene glycol and heated the oil bath to 125° C. for 19 hours. Concentrated free of solvent, then purified the residue using silica gel chromatography and an ethyl acetate-hexane gradient. This gave 147 of pyrrole as a yellow oil. It was dissolved in 2 mL ethanol and added into a vial along with 32 mg squaric acid. The vial was sealed and its contents stirred and heated at 80° C. for 2 hours. The solution was cooled, filtered, and the filter cake washed with ethanol then dried under vacuum to 113 mg squaraine product. $^1$H NMR (400 MHz, Chloroform-d) δ 7.84-7.78 (m, 1H), 7.74 (t, J=9.4 Hz, 2H), 7.56 (s, 1H), 7.48-7.42 (m, 2H), 7.40 (s, 1H), 7.24 (d, J=8.4 Hz, 1H), 4.87 (t, J=6.5 Hz, 2H), 3.27 (t, J=6.5 Hz, 2H), 2.53 (d, J=6.9 Hz, 2H), 1.96 (d, J=7.8 Hz, 4H). $^{13}$C NMR (101 MHz, Chloroform-d) δ 159.39, 136.24, 134.33, 133.49, 132.28, 131.33, 128.00, 127.87, 127.69, 127.59, 127.47, 126.03, 125.52, 50.76, 38.95, 28.69, 24.90, 24.80. LC-MS (APCI, +) 601. Amorphous polycarbonate film: λ max=592 nm/FWHM=26 nm.

Example 1.14 (Synthesis of SQL-14)

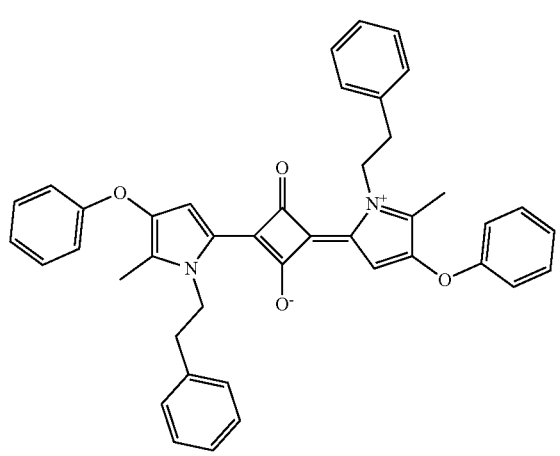

SQL-14

175 mg 2-methyl-3-phenoxy-1-(2-phenylethyl)-1H-pyrrole was synthesized as described in the literature (M. Beller et. al., J. Am. Chem. Soc., 2013, 135(30), 11384-11388). It was dissolved in 3 mL ethanol and added into a vial along with 32 mg squaric acid. The vial was sealed and the contents stirred and heated at 80° C. for 1 hour. After cooling to room temperature, it took 10 minutes for a slurry to develop. This was filtered, washed with ethanol, and dried under vacuum at 70° C. to 42 mg of squaraine product. $^1$H NMR (400 MHz, Chloroform-d) δ 7.46 (s, 1H), 7.38-7.19 (m, 4H), 7.14 (dd, J=6.4, 1.7 Hz, 2H), 7.09 (ddt, J=8.5, 7.4, 1.1 Hz, 1H), 7.04-6.94 (m, 2H), 4.88 (t, J=6.7 Hz, 2H), 3.11 (t, J=6.7 Hz, 2H), 1.85 (s, 3H). $^{13}$C NMR (101 MHz, Chloroform-d) δ 157.74, 144.79, 138.83, 138.13, 129.71, 129.25, 128.62, 126.91, 123.94, 122.97, 116.76, 49.28, 38.64, 9.47. LC-MS (APCI, −) 632. Polymethylmethacrylate film: λ max=591 nm, FWHM=36 nm.

Example 1.15 (Synthesis of SQL-15)

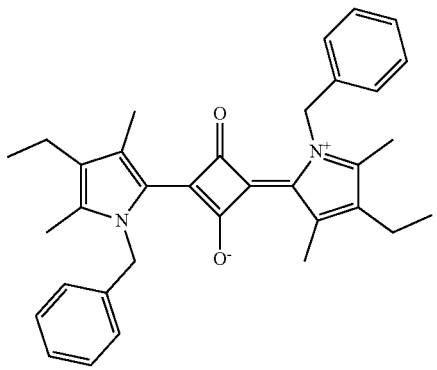

SQL-15

Pulverized 2.39 g potassium hydroxide then quickly transferred it to a reactor containing an argon atmosphere. Dissolved 1.00 g 3-ethyl-2,4-dimethylpyrrole in 15 mL dimethylsulfoxide and added to the reactor. Stirred the resulting slurry for 1 hour then cooled with an icebath while dripping in 1.39 g benzyl bromide over 1 minute. Stirred for 1 hour, then poured onto ice, extracted with hexanes, washed the extract 3 times with water, dried it with sodium sulfate, and concentrated to 2.20 g brown oil. This contained several impurities along with the desired pyrrole product but was used without further purification. 600 mg of this oil was dissolved in 5 mL ethanol and added to a vial along with 145 mg squaric acid. The vial was sealed and heated at 80° C. for 2 hours, then cooled and filtered. The filter cake was washed with ethanol and dried under vacuum at 70° C. to 64 mg of solid. This was further purified using silica gel chromatography with dichloromethane eluent to provide 35 mg of pure product squaraine. $^1$H NMR (400 MHz, Chloroform-d) δ 7.08 (d, J=6.7 Hz, 3H), 6.75 (d, J=6.8 Hz, 2H), 5.90 (s, 2H), 2.53 (s, 3H), 2.34 (q, J=7.6 Hz, 2H), 2.10 (s, 3H), 0.96 (t, J=7.6 Hz, 3H). $^{13}$C NMR (101 MHz, Chloroform-d) δ 176.99, 174.22, 145.34, 138.37, 135.78, 130.65, 128.59, 127.41, 126.84, 125.89, 50.13, 17.69, 14.83, 12.23, 11.35. HPLC-MS (APCI, −) 504. Amorphous polycarbonate film: λ max=595 nm, FWHM=33 nm.

Example 1.16 (Synthesis of SQL-16)

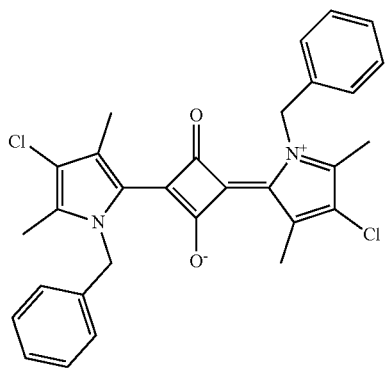

SQL-16

116 mg 4-Chloro-3,5-dimethyl-1H-pyrrole-2-carboxylic acid was made according to published methods. It was stirred in 2 mL trifluoroacetic acid for 5 minutes. The solution was concentrated then 10 mL toluene was added and this solution was concentrated. Dissolved the residue in 2 mL dimethylsulfoxide and transferred it onto 186 mg of pulverized potassium hydroxide in a reactor under argon. Stirred the resulting slurry for 1 hour then cooled in an icebath and dripped in 114 mg benzyl bromide over 1 minute. Stirred the solution for 30 minutes then diluted it with water and extracted it with hexanes. Washed the extract with water, dried it with sodium sulfate, and concentrated it to 129 mg yellow oil. Dissolved the oil in 1 mL ethanol and added it to a vial along with 33 mg squaric acid. Sealed the vial then stirred the contents and heated at 80° C. for 1 hour. Cooled the slurry, filtered it, and washed the filter cake with ethanol. Dried at 60° C. under vacuum to 22 mg solid squaraine product. $^1$H NMR (400 MHz, Chloroform-d) δ 7.25-7.17 (m, 3H), 6.90-6.84 (m, 2H), 6.01 (s, 2H), 2.67 (s, 3H), 2.29 (s, 3H). $^{13}$C NMR (101 MHz, Chloroform-d) δ 177.55, 175.68, 144.11, 137.28, 134.81, 128.80, 127.31, 126.33, 125.89, 119.84, 51.28, 12.62, 11.50. HPLC-MS (APCI, −) 516. Amorphous polycarbonate film: λ max=597 nm, FWHM=34 nm.

Example 1.17 (Synthesis of SQL-17)

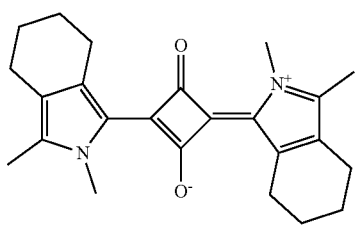

SQL-17

430 mg 4,5,6,7-Tetrahydro-1-methyl-2H-isoindole was synthesized as described in the literature (Kancharla, Papireddy et. al., J. Med. Chem., 58(18), 7286-7309; 2015). This was dissolved in 8 mL dimethylsulfoxide and added onto 1.00 g pulverized potassium hydroxide in an argon-flushed reactor. This slurry was stirred for 45 minutes then cooled in an icebath while 0.4 mL methyl iodide was dripped in over 1 minute. Cooling was removed and the reaction stirred for 50 minutes. Added water, extracted with hexanes, washed the extract with water then dried it with sodium sulfate, and concentrated to 450 mg yellow oil. This was dissolved in 6 mL ethanol and added into a vial along with 172 mg squaric acid. The vial was sealed and its contents stirred and heated to 80° C. for 2 hours. Cooled the slurry, filtered, and washed the filter cake with ethanol. Dried the cake to 255 mg of squaraine product. $^1$H NMR (400 MHz, Chloroform-d) δ 4.08 (s, 3H), 3.23 (d, J=5.2 Hz, 2H), 2.41 (d, J=5.2 Hz, 2H), 2.24 (s, 3H), 1.76 (h, J=3.1 Hz, 4H). $^{13}$C NMR (101 MHz, Chloroform-d) δ 171.85, 144.27, 137.59, 126.11, 125.08, 34.40, 24.90, 23.26, 22.84, 21.74, 11.10. LC-MS (APCI, −) 375. Amorphous polycarbonate film: λ max=599 nm, FWHM=35 nm.

Example 1.18 (Synthesis of SQL-18)

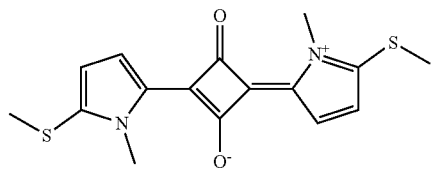

SQL-18

440 mg of 1-methyl-2-(methylthio)pyrrole was prepared as described in the literature (Nedolya, N. et. al. Synthesis, 45(1), 93-100; 2013). It was dissolved in 5 mL ethanol and combined with 197 mg squaric acid in a vial. The vial was sealed and its contents stirred and heated to 80° C. for 1 hour. The slurry was cooled and filtered. The filter cake was washed with ethanol and dried under vacuum at 70° C. to 270 mg of squaraine product. $^1$H NMR (400 MHz, Chloroform-d) δ 7.82 (d, J=4.5 Hz, 1H), 6.40 (d, J=4.5 Hz, 1H), 4.17 (d, J=1.6 Hz, 3H), 2.61 (d, J=1.6 Hz, 3H). $^{13}$C NMR (101 MHz, Chloroform-d) δ 147.91, 130.18, 123.96, 113.52, 34.75, 16.00. LC-MS (APCI, −) 332. Amorphous polycarbonate film: λ max=614 nm, FWHM=42 nm.

Example 1.19 (Synthesis of SQL-19)

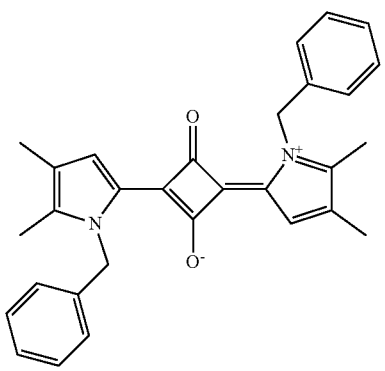

SQL-19

401 mg 1-benzyl-2,3-dimethylpyrrole was synthesized as described in the literature (Gabriele, B et. al. J. Org. Chem., 68(20), 7853-7861; 2003). This was dissolved in 8 mL ethanol and added into a vial along with 123 mg squaric acid. The vial was sealed and its contents stirred and heated at 80° C. for 2 hours. Once cooled, the slurry was filtered and the filter cake washed with ethanol and vacuum dried at 70° C. to 183 mg of squaraine product. $^1$H NMR (400 MHz, Chloroform-d) δ 7.64 (s, 1H), 7.26 (d, J=21.2 Hz, 3H), 7.00 (d, J=7.5 Hz, 2H), 6.01 (s, 2H), 2.17 (s, 3H), 2.08 (s, 3H). $^{13}$C NMR (101 MHz, Chloroform-d) δ 145.69, 137.78, 128.75, 128.10, 127.19, 125.09, 126.18, 50.83, 11.52, 11.35. LC-MS (APCI, +) 449. Amorphous polycarbonate film: λ max=581 nm, FWHM=26 nm.

Example 1.20 (Synthesis of SQL-20)

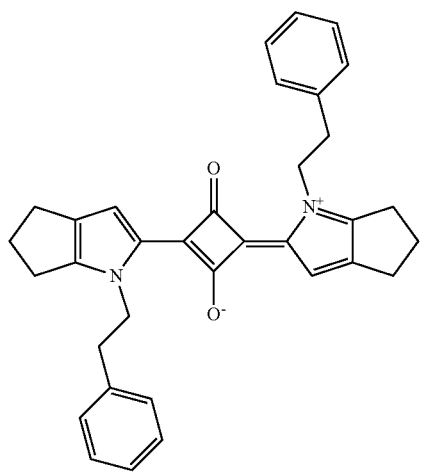

SQL-20

300 mg 1-phenethyl-1,4,5,6-tetrahydrocyclopenta[b]pyrrole was synthesized as described in the literature (M. Beller et. al., J. Am. Chem. Soc., 2013, 135(30), 11384-11388). It was dissolved in 5 mL ethanol and combined with 80 mg squaric acid in a vial. The vial was sealed and its contents stirred and heated at 80° C. for 2 hours then cooled and filtered. The filter cake was washed with ethanol and dried under vacuum at 70° C. to 197 mg of squaraine product. This was further purified using silica gel chromatography and a methanol-dichloromethane gradient to give 120 mg. $^1$H NMR (400 MHz, Chloroform-d) δ 7.41 (s, 1H), 7.20-7.09 (m, 3H), 6.99-6.91 (m, 2H), 4.69 (t, J=6.5 Hz, 2H), 3.01 (t, J=6.5 Hz, 2H), 2.51 (t, J=7.1 Hz, 2H), 2.10 (p, J=7.0 Hz, 2H), 1.96 (d, J=10.5 Hz, 2H). $^{13}$C NMR (101 MHz, Chloroform-d) δ 159.28, 138.84, 134.18, 131.30, 129.33, 128.42, 126.67, 50.86, 38.75, 28.88, 24.85, 24.83. LC-MS (APCI, +) 501. Amorphous polycarbonate film: λ max=591 nm, FWHM=25 nm.

Example 1.21 (Synthesis of SQL-21)

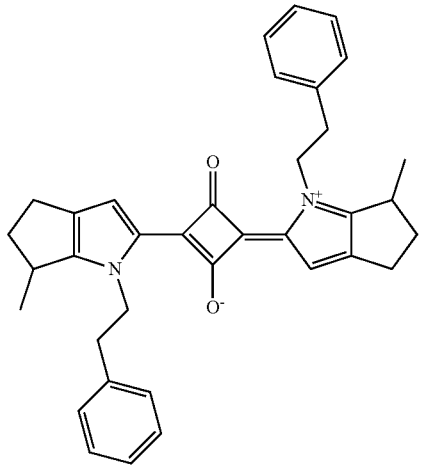

SQL-21

Established an argon atmosphere within a reactor, then added 2.00 g 1-methylcyclopentanone and 35 mL 3-methyl-3-pentanol. Stirred and added 2.72 g phenethylamine. Heated this mixture in an 80° C.-oil bath for 40 minutes then added 250 mg dichloro(p-cymene)ruthenium(II) dimer, 476 mg XantPhos, and 2.50 mL ethylene glycol. Heated the oil bath to 125° C. for 18 hours. Cooled, concentrated, and purified the residue using silica gel chromatography and an ethyl acetate-hexanes gradient. The product pyrrole eluted along with an impurity, but was used without further purification after concentrating it to 880 mg of yellow oil. This was dissolved in 10 mL ethanol and heated at 80° C., stirred, in a sealed vial along with 222 mg squaric acid. After 2 hours, the mixture was cooled, concentrated and purified using silica gel chromatography and a methanol-dichloromethane gradient, giving 1.16 g of product squaraine. $^1$H NMR (400 MHz, Chloroform-d) δ 7.51 (s, 1H), 7.31-7.18 (m, 3H), 7.12 (ddd, J=7.5, 4.7, 1.7 Hz, 2H), 5.33 (dt, J=13.5, 6.1 Hz, 1H), 4.33 (dt, J=13.4, 7.8 Hz, 1H), 3.10 (dd, J=7.9, 6.2 Hz, 2H), 2.73-2.60 (m, 1H), 2.58-2.46 (m, 1H), 2.45-2.33 (m, 2H), 1.89 (tt, J=8.4, 4.2 Hz, 1H), 1.19-1.12 (m, 3H). HPLC-MS (APCI, +) 529. $^{13}$C NMR (101 MHz, Chloroform-d) δ 162.04, 161.93, 138.68, 133.96, 133.93, 131.58, 129.27, 128.46, 126.67, 49.94, 49.90, 38.93, 38.46, 38.44, 32.95, 32.90, 23.35, 18.69. Amorphous polycarbonate film: λ max=593 nm, FWHM=24 nm.

Example 1.22 (Synthesis of SQL-22)

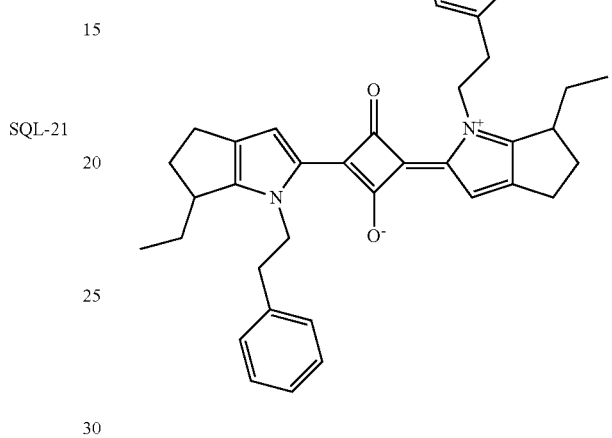

SQL-22

0.50 g 2-ethylcyclopentanone and 10 mL 1-methylcyclohexanol were combined in a reactor and an argon atmosphere established. 0.60 g phenethylamine was added and the mixture was stirred and heated in an 80° C.-oil bath for 30 minutes. 27 mg dichloro(p-cymeme)ruthenium (II) dimer, 52 mg XantPhos, and 0.55 mL ethylene glycol were added and the oil bath was heated to 145° C. for 24 hours. The solution was concentrated mostly free of 1-methylcyclohexanol and the residue purified by silica gel chromatography using an ethyl acetate-hexanes gradient. The 209 mg of pyrrole product contained an impurity, but was used without further purification. It was dissolved in 3 mL ethanol and combined in a vial along with 22 mg squaric acid. The vials contents were stirred and the vial was sealed and heated at 80° C. for 2 hours. Concentrated the resulting solution and purified it using silica gel chromatography and an ethyl acetate-hexanes gradient, giving 93 mg. This was mixed with isopropanol and filtered to provide an easily-handled solid that was dried to 57 mg of squaraine product. $^1$H NMR (400 MHz, Chloroform-d) δ 7.52 (s, 1H), 7.25 (q, J=7.7 Hz, 3H), 7.10 (t, J=6.1 Hz, 2H), 5.51-5.37 (m, 1H), 4.24 (dq, J=21.4, 13.0, 10.3 Hz, 1H), 3.09 (dt, J=11.8, 8.0 Hz, 2H), 2.63 (dt, J=15.2, 7.5 Hz, 1H), 2.51 (ddt, J=15.8, 8.7, 4.3 Hz, 1H), 2.33-2.25 (m, 1H), 2.22 (d, J=18.2 Hz, 1H), 2.09-1.94 (m, 1H), 1.64 (s, 1H), 1.50-1.37 (m, 1H), 0.87 (dt, J=9.7, 4.9 Hz, 3H). $^{13}$C NMR (101 MHz, Chloroform-d) δ 161.16, 161.04, 138.77, 134.53, 134.50, 131.72, 129.27, 129.26, 128.45, 126.66, 50.19, 50.13, 39.55, 38.90, 35.03, 26.06, 23.63, 11.44, 11.42. HPLC-MS (APCI, +) 557. Amorphous polycarbonate film: λ max=594 nm, FWHM=25 nm.

Example 1.23 (Synthesis of SQL-23)

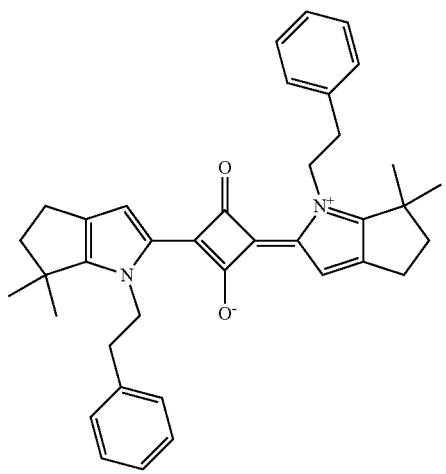

SQL-23

To a reactor, under argon, was added 0.56 g 2,2-dimethylcyclopentanone and 9 mL 3-methyl-3-pentanol. This solution was stirred, 665 mg phenethylamine added, and the resulting mixture heated in an 80° C.-oil bath for 30 minutes. 61 mg dichloro(p-cymene)ruthenium (II) dimer, 115 mg XantPhos, and 0.61 mL ethylene glycol were added and the oil bath heated to 125° C. for 45 hours. The solution was concentrated and purified by silica gel chromatography using an ethyl acetate-hexanes gradient, providing 176 mg of impure pyrrole product. This was dissolved in 2 mL ethanol and combined with 42 mg squaric acid in a vial. The solution was stirred and the vial sealed and heated at 80° C. for 2 hours. The resulting slurry was cooled and filtered. The filter cake was washed with ethanol and dried at 70° C. under vacuum to 98 mg of squaraine product. $^1$H NMR (400 MHz, Chloroform-d) δ 7.55 (s, 1H), 7.44-7.36 (m, 2H), 7.32 (t, J=7.4 Hz, 2H), 7.25 (t, J=7.1 Hz, 1H), 4.81 (dd, J=9.8, 6.5 Hz, 2H), 3.20-3.06 (m, 2H), 2.65 (t, J=7.0 Hz, 2H), 2.27 (t, J=7.0 Hz, 2H), 1.37 (s, 6H). $^{13}$C NMR (101 MHz, Chloroform-d) δ 170.72, 162.46, 138.37, 133.80, 131.95, 129.26, 128.60, 126.64, 49.27, 47.00, 40.67, 39.53, 26.82, 22.51. HPLC-MS (APCI, +) 557. Amorphous polycarbonate film: λ max=594 nm, FWHM=24 nm.

Example 1.24 (Synthesis of SQL-24)

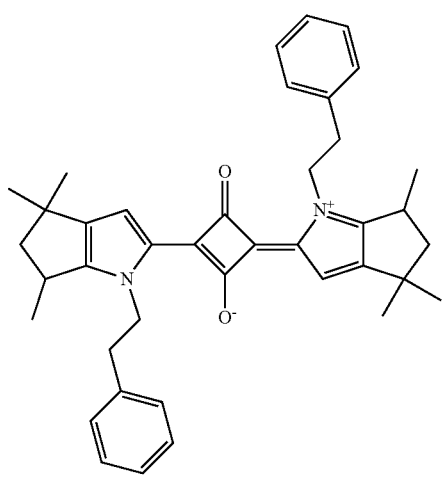

SQL-24

Under argon, a reactor was loaded with 0.53 g 2,4,4-trimethylcyclopentanone and 10 mL 3-methyl-3-pentanol. This was stirred, 0.56 g phenethylamine was added, and the solution heated in an 80° C.-oil bath for 0.5 hours. 51 mg dichloro(p-cymene)ruthenium (II) dimer, 97 mg XantPhos, and 0.51 mL ethylene glycol were added and the oil bath heated to 125° C. for 23 hours. Concentrated the reaction solution and purified the residue by silica gel chromatography using an ethyl acetate-hexanes gradient to give 19 mg of a mixture of 2 compounds that containing the desired pyrrole. This was combined with 0.3 mL ethanol and 4.3 mg squaric acid in a vial. The vial contents were stirred and heated at 80° C. for 2 hours. The slurry was cooled and filtered. The filter cake was washed with ethanol and dried under vacuum at 70° C. to 2.5 mg of squaraine product. $^1$H NMR (400 MHz, Chloroform-d) δ 7.51 (s, 1H), 7.25 (dd, J=5.0, 2.0 Hz, 3H), 7.08 (dq, J=7.5, 2.8 Hz, 2H), 5.37 (dt, J=13.5, 5.7 Hz, 1H), 4.32 (dt, J=14.2, 7.8 Hz, 1H), 3.11 (dd, J=7.7, 5.6 Hz, 2H), 2.20 (t, J=10.4 Hz, 2H), 1.72 (dd, J=12.4, 6.3 Hz, 1H), 1.28 (s, 3H), 1.16 (q, J=4.9, 3.1 Hz, 6H). $^{13}$C NMR (101 MHz, Chloroform-d) δ 143.61, 129.26, 128.50, 126.68, 54.75, 49.66, 38.90, 37.76, 32.33, 29.92, 29.47, 18.95. HPLC-MS (APCI, +) 585. Amorphous polycarbonate film: λ max=592 nm/FWHM=25 nm.

Example 1.25 (Synthesis of SQL-25)

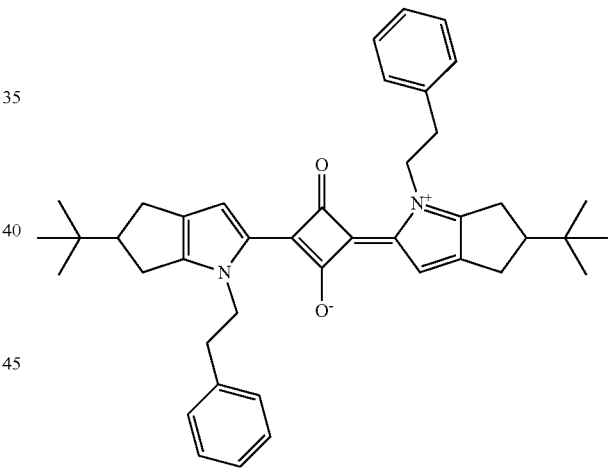

SQL-25

500 mg 3-t-butylcyclopentanone was synthesized as described in the literature. This was dissolved in 9 mL 3-methyl-3-pentanol and added to a reactor under argon. 475 mg phenethylamine was added and the solution heated in an 80° C.-oil bath for 30 minutes. 44 mg dichloro(p-cymene)ruthenium (II) dimer, 82 mg XantPhos, and 0.44 mL ethylene glycol were added and the oil bath heated to 130° C. for 17 hours. Concentrated the reaction solution and purified the residue by silica gel chromatography using an ethyl acetate-hexanes gradient. 382 mg of a mixture of products containing the desired pyrrole was obtained. It was dissolved in 5 mL ethanol and combined with 82 mg squaric acid in a vial. The vial was sealed and its contents stirred and heated at 80° C. for 2 hours. The slurry was cooled and filtered. The filter cake was dried under vacuum at 80° C. to 49 mg of product squaraine. $^1$H NMR (400 MHz, Chloroform-d) δ 7.43 (d, J=32.4 Hz, 1H), 7.14 (qd, J=7.0, 5.8, 3.1 Hz, 3H), 6.93 (dq, J=10.1, 3.9, 3.0 Hz, 2H), 4.74 (dt, J=12.6, 6.0 Hz, 1H), 4.64 (dt, J=13.2, 6.4 Hz, 1H), 3.02 (q, J=6.5 Hz, 2H), 2.46 (p, J=8.4, 7.3 Hz, 1H), 2.29 (dq, J=14.2, 8.8 Hz, 1H), 1.84 (s, 1H), 0.82 (s, 4H), 0.71 (s, 5H). $^{13}$C NMR (101 MHz, Chloroform-d) δ 158.24, 138.96, 133.13, 130.66, 129.38, 129.32, 128.49, 128.47, 128.46, 126.76, 126.59, 55.68, 50.84, 50.69, 49.98, 38.78, 33.64, 32.47, 31.03, 27.35, 27.29, 26.83, 26.70, 24.44. HPLC-MS (APCI, +) 613. Amorphous polycarbonate film: λ max=593 nm, FWHM=24 nm.

Example 1.26 (Synthesis of SQL-26)

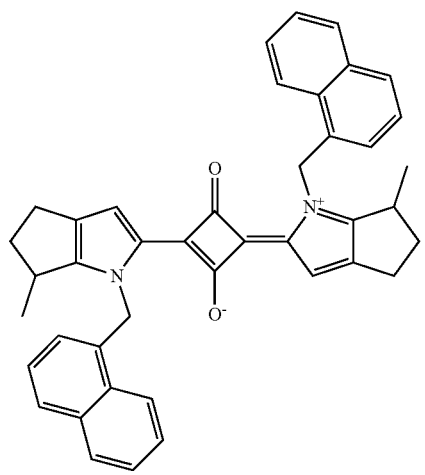

SQL-26

0.42 g 2-methylcyclopentanone was dissolved in 10 mL 1-methylcyclohexanol under argon. 0.74 g 1-naphthylmethylamine was added and the resulting solution heated in an 80° C.-oil bath for 40 minutes. 26 mg dichloro(p-cymene)ruthenium (II) dimer, 50 mg XantPhos, and 0.53 mL ethylene glycol were added and the oil bath heated to 145° C. for 24 hours. Concentrated free of most 1-methylcyclohexanol then purified the residue using silica gel chromatography with an ethyl acetate-hexanes gradient. This provided 180 mg of pyrrole product which was dissolved with 2.5 mL ethanol and added to 39 mg squaric acid in a vial. The vial was sealed and its contents stirred and heated at 80° C. for 2.5 hours. The resulting slurry was cooled and filtered. The filter cake was dried under vacuum at 75° C. to 148 mg of squaraine product. HPLC-MS (APCI, +) 601. Amorphous polycarbonate film: λ max=594 nm, FWHM=23 nm.

Example 1.27 (Synthesis of SQL-27)

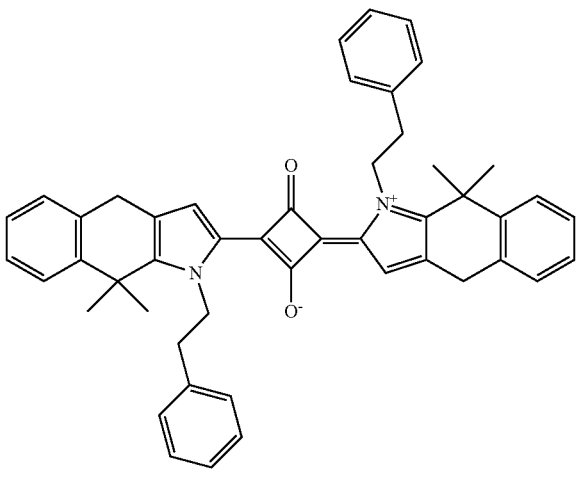

SQL-27

1.23 g 1,1-dimethyl-2-tetralone was synthesized as described in the literature. It was dissolved in 15 mL 3-methyl-3-pentanol and added to a reactor under argon. 1.03 g phenethylamine was added and the solution stirred and heated in an 80° C. oil bath for 35 minutes. Added 94 mg dichloro(p-cymene)ruthenium (II) dimer, 178 mg XantPhos, and 0.95 mL ethylene glycol and increased the oil bath to 140° C. for 23 hours. Concentrated and purified the residue with silica gel chromatography using an ethyl acetate-hexanes gradient. 149 mg of a mixture containing the pyrrole product was obtained. This was further purified using a dichloromethane-hexanes gradient, giving 99 mg of pure pyrrole product. This was dissolved in 1.5 mL ethanol and combined with 20 mg squaric acid in a vial. The vial was sealed and its contents stirred and heated at 80° C. for 2 hours. The slurry was cooled and filtered. The filter cake was washed with ethanol and dried under vacuum to 40 mg of squaraine product. $^1$H NMR (400 MHz, Chloroform-d) δ 7.94 (s, 1H), 7.53 (dd, J=14.5, 7.7 Hz, 3H), 7.43-7.27 (m, 7H), 4.09 (s, 2H), 3.18 (s, 2H), 1.85 (s, 6H). Amorphous polycarbonate film: λ max=597 nm, FWHM=27 nm.

Example 1.28 (Synthesis of SQL-28)

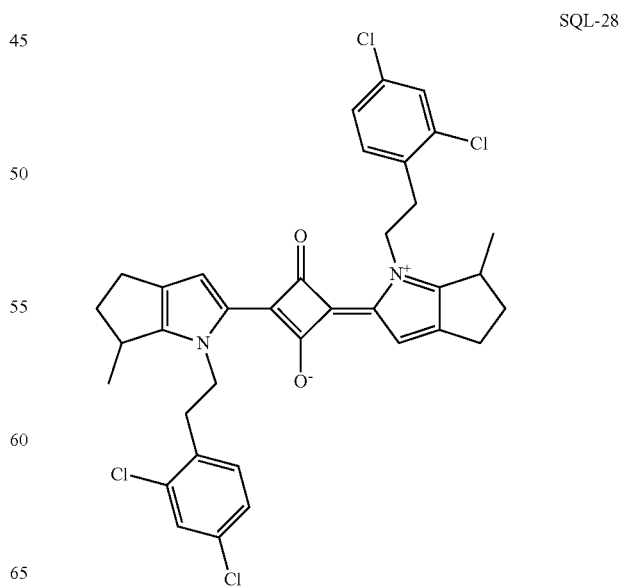

SQL-28

0.52 g 2-methylcyclopentanone and 10 mL 1-methylcyclohexanol were combined in a reactor under argon and stirred. 1.11 g 2,4-dichlorophenethylamine was added and the solution heated in an 80° C. oil bath for 30 minutes. 32 mg dichloro(p-cymene)ruthenium (II) dimer, 61 mg Xant-Phos, and 0.66 mL ethylene glycol were added and the oil bath heated to 145° C. for 6 hours. Concentrated free of most 1-methylcyclohexanol then purified the residue using silica gel chromatography and an ethyl acetate-hexanes gradient. The 414 mg of pyrrole product eluted with an impurity, but was used without further purification. It was dissolved in 3 mL ethanol and combined with 81 mg squaric acid in a vial. The vial was sealed and its contents stirred and heated at 80° C. for 2 hours. The slurry was cooled and filtered. The filter cake was washed with ethanol and dried at 70° C. under vacuum to 361 mg of squaraine product. $^1$H NMR (400 MHz, Chloroform-d) δ 7.50 (s, 1H), 7.40 (q, J=1.5 Hz, 1H), 7.15-7.10 (m, 2H), 5.34 (tdd, J=15.2, 7.4, 4.9 Hz, 1H), 4.39-4.25 (m, 1H), 3.37-3.25 (m, 1H), 3.15 (dtd, J=13.5, 7.7, 2.0 Hz, 1H), 2.75-2.64 (m, 1H), 2.67-2.51 (m, 1H), 2.54-2.38 (m, 1H), 1.94 (dddd, J=12.7, 7.4, 5.4, 3.3 Hz, 1H), 1.21 (dd, J=7.0, 1.6 Hz, 3H). HPLC-MS (APCI, +) 667. Amorphous polycarbonate film: λ max=594 nm, FWHM=24 nm.

Example 2.1 Fabrication of Filter Layer

A glass substrate was prepared in substantially the following manner. A 1.1 mm thick glass substrate measuring 1 inch×1 inch was cut to size. The glass substrate was then washed with detergent and DI water, rinsed with fresh DI water and sonicated for about 1 hour. The glass was then soaked in isopropanol (IPA) and sonicated for about 1 hour. The glass substrate was then soaked in acetone and sonicated for about 1 hour. The glass was then removed from the acetone bath and dried with nitrogen gas at room temperature.

A 25 wt % solution of Poly(methyl methacrylate) (PMMA) average M.W. 120,000 by GPC from Sigma Aldrich) copolymer in cyclopentanone (99.9% pure) was prepared. The prepared copolymer was stirred for overnight at 40° C. [PMMA] CAS: 9011-14-7; [Cyclopentanone] CAS: 120-92-3.

4 gram of 25% PMMA solution prepared above was added to 3 mg of squarylium compound made as described above in a sealed container and mixed for about 30 minutes. The PMMA/Chromophore solution was then spin coated onto a prepared glass substrate at 1000 RPM for 3 s; then 1500 RPM for 20 s and then 500 RPM for 2 s. The resulting wet coating was about a thickness of 10 μm. The samples were covered with aluminum foil before spin coating to protect them from exposure to light. 3 samples each were prepared in this manner for optical properties study. The spin coated samples were baked in a vacuum oven at 80° C. for 3 hours to evaporate the remaining solvent.

Figure 2:
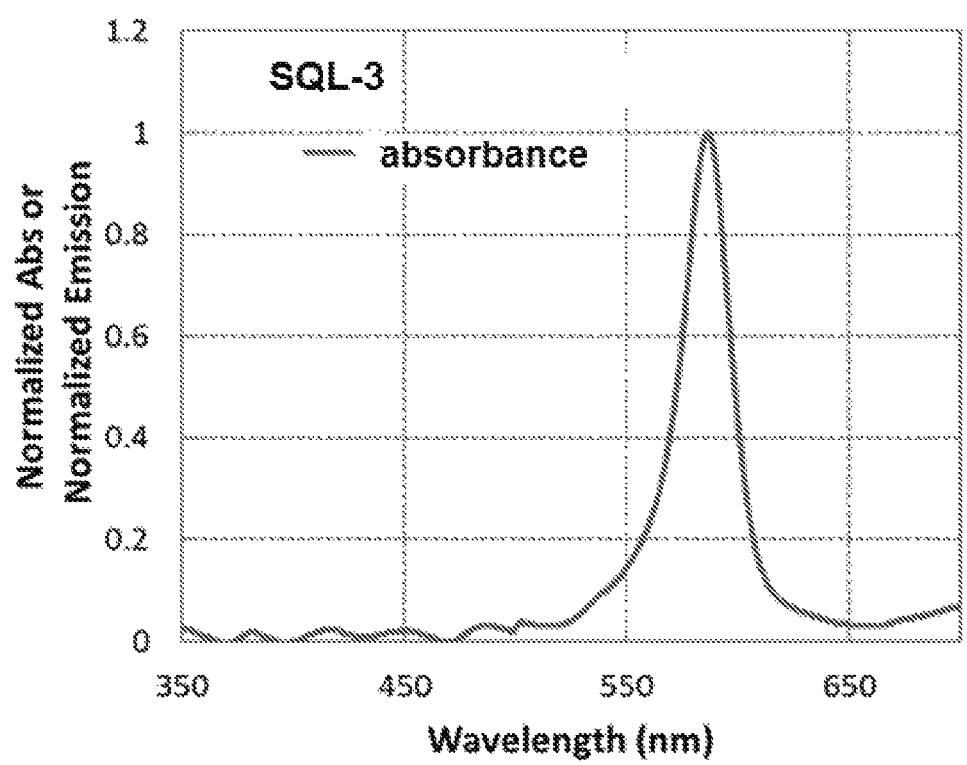
FIG. 2 is a graph depicting the normalized absorption and emission spectra of a film comprising SQL-3.
Figure 3:
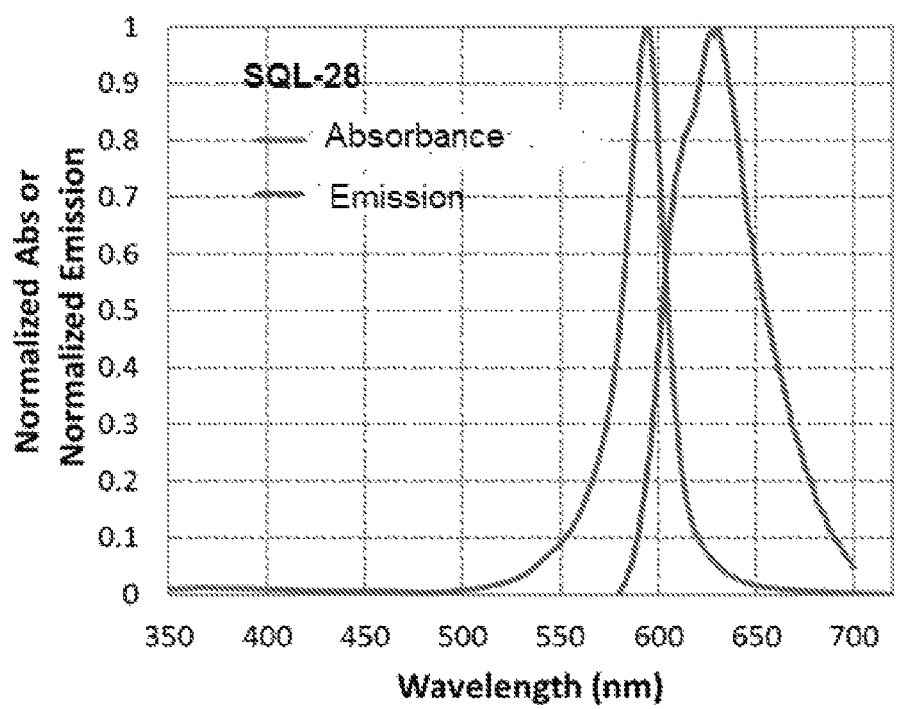
FIG. 3 is a graph depicting the normalized absorption and emission spectra of a film comprising SQL-28 (APC).
Figure 4:
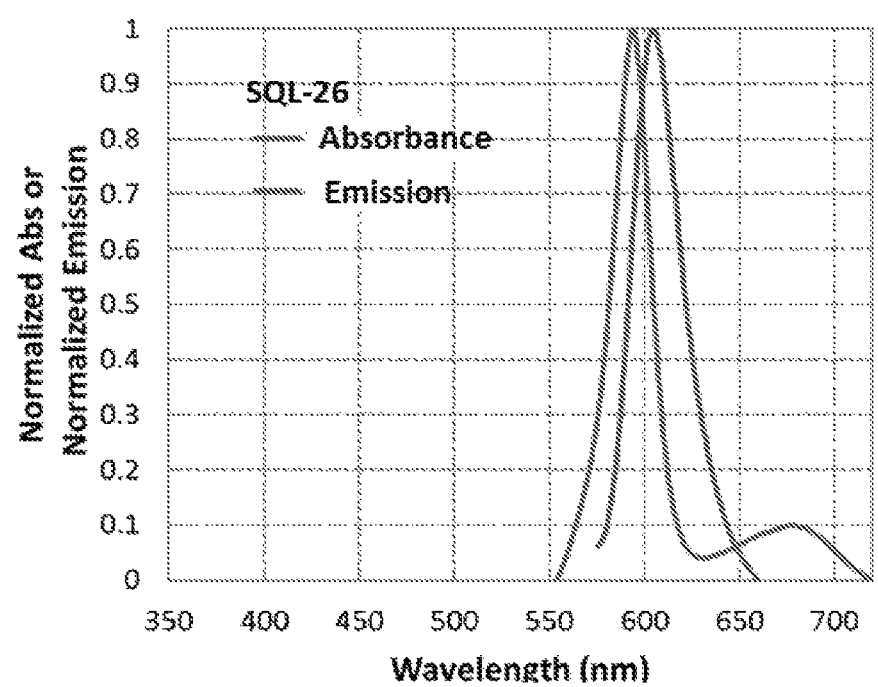
FIG. 4 is a graph depicting the normalized absorption and emission spectra of a film comprising SQL-26
Figure 5:
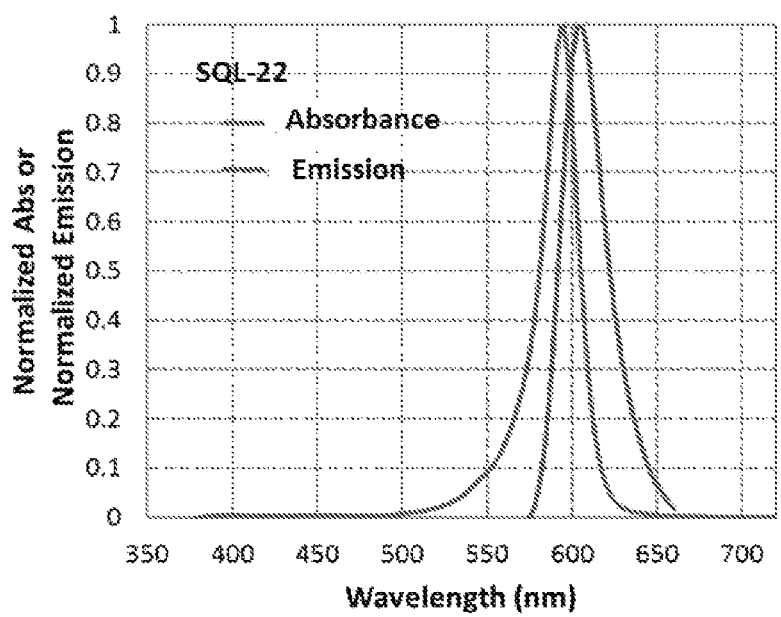
FIG. 5 is a graph depicting the normalized absorption and emission spectra of a film comprising SQL-22
Figure 6:
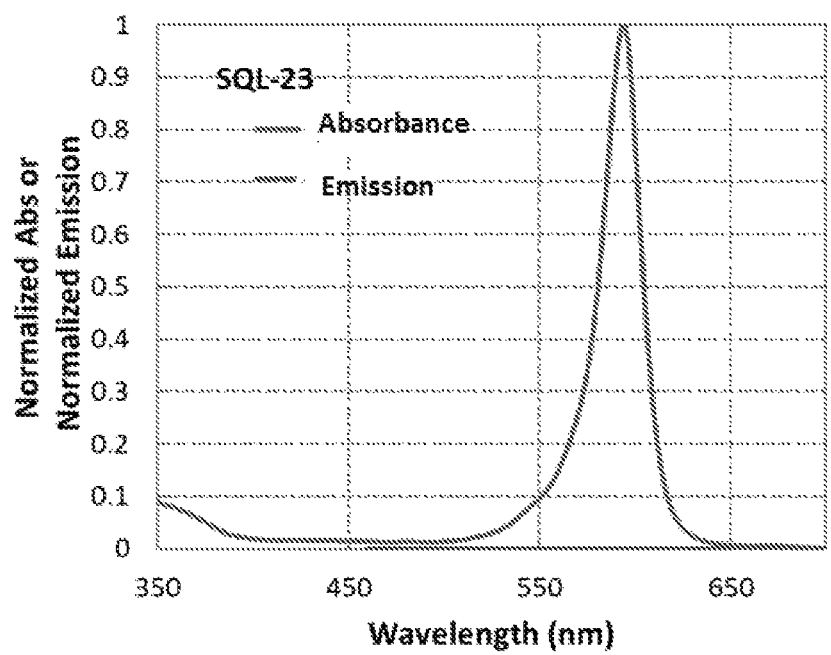
FIG. 6 is a graph depicting the normalized absorption and emission spectra of a film comprising SQL-23
Figure 7:
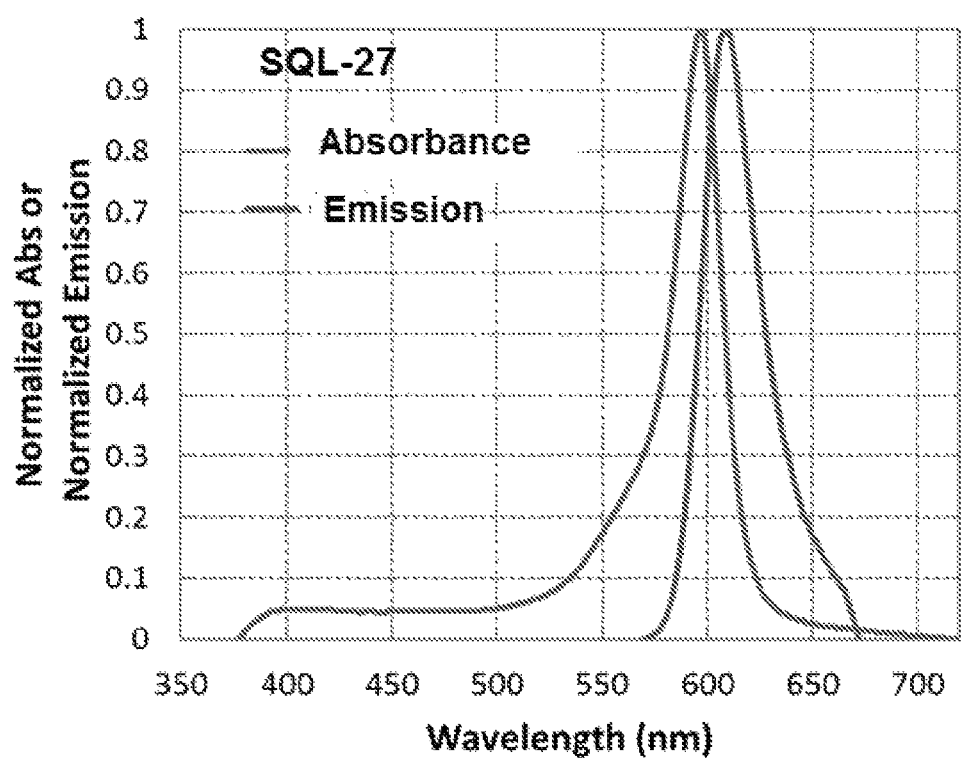
FIG. 7 is a graph depicting the normalized absorption and emission spectra of a film comprising SQL-27

The 1 inch×1 inch sample was inserted into a Shimadzu, UV-3600 UV-VIS-NIR spectrophotometer (Shimadzu Instruments, Inc., Columbia, Md., USA). The resulting absorption spectrum of a film comprising SQL-3 (from Example 1.3) is shown in FIG. 2. The maximum absorption was normalized at about 100% at the perceived maximum absorbance wavelength, and the half-value width (FWHM) at the maximum absorption was measured.

FIG. 3, FIG. 4, FIG. 5, FIG. 6, and FIG. 7 show absorbance and emission spectral data for films comprising SQL-28, SQL-26, SQL-22, SWL-23 and SQL-27, respectively.

The fluorescence spectrum of a 1 inch×1 inch film sample prepared as described above was determined using a Fluorolog spectrofluorometer (Horiba Scientific, Edison, N.J., USA) with the excitation wavelength set a the respective maximum absorbance wavelength.

The quantum yield of a 1 cm×1 cm sample prepared as described above were determined using a Quantarus-QY spectrophotometer (Hamamatsu Inc., Campbell, Calif., USA) set at the respective maximum absorbance wavelength. The quenching compounds of the invention were weakly fluorescent or essentially non-fluorescent.

The absorbance maximum lifetime was determined by placing a 1 inch by 1 inch film sample (film with SQL-1) in a vacuum at 80° C. and periodically checking the absorbance of the sample in ambient environmental pressure and returning to a vacuum/*) C environment. After 527 hours, the absorbance was about 87% of the original absorbance (see table 1). In another example, a 1 inch by 1 inch sample was placed in ambient air at 85° C. After 509.5 hours, the absorbance was about 80% and 64% as indicated in Table 1.

The results of the film characterization (absorption peak wavelength and FWHM and quantum yield) are shown in Table 1 below.

TABLE 1

| Cmpd | Structure | Peak absorption (nm) | FWHM (nm) | φ |
|---|---|---|---|---|
| SQL-1 | 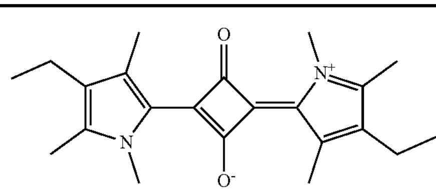 | 596 nm (APC) | 34 | |
| SQL-2 | 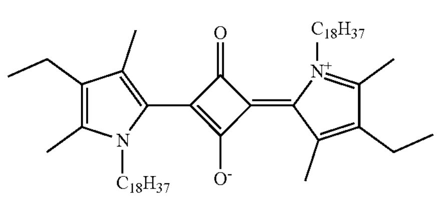 | 595 nm (APC) | 35 | 0.052 |

TABLE 1-continued

| Cmpd | Structure | Peak absorption (nm) | FWHM (nm) | φ |
|---|---|---|---|---|
| SQL-3 | 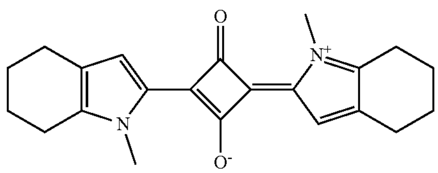 [SMILES: Cn1c(C2=C([O-])/C(=C3\C=C4CCCCC4=[N+]3C)C2=O)cc2c1CCCC2] | 582 nm (APC) | 26 | |
| SQL-4 | 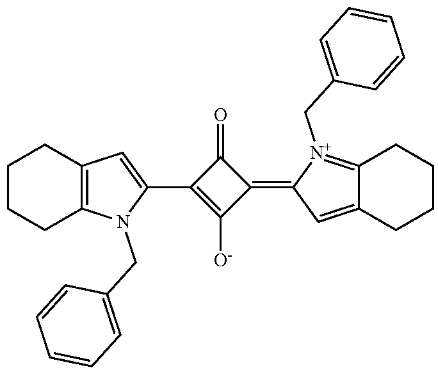 [SMILES: O=C1C(c2cc3c(n2Cc2ccccc2)CCCC3)=C([O-])/C1=C1\C=C2CCCCC2=[N+]1Cc1ccccc1] | 585 nm (APC) | 26 | |
| SQL-5 | 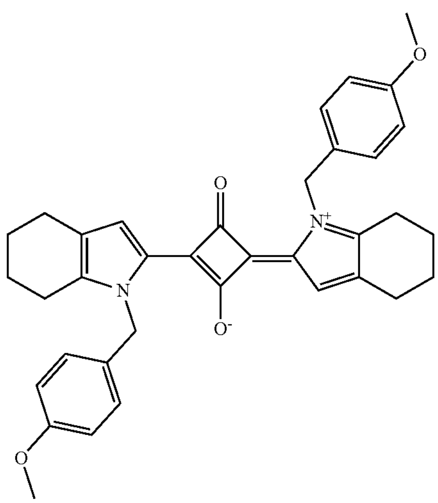 [SMILES: COc1ccc(Cn2c(C3=C([O-])/C(=C4\C=C5CCCCC5=[N+]4Cc4ccc(OC)cc4)C3=O)cc3c2CCCC3)cc1] | 585 nm (APC) | 27 | |
| SQL-6 | 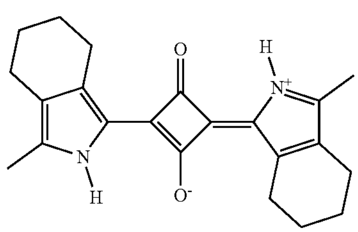 | 575 nm (APC) | 26 nm | |
| SQL-7 | 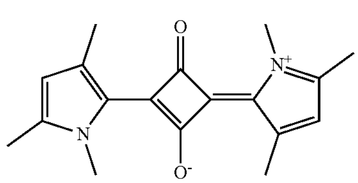 | 585 nm (APC) | 40 nm | |

TABLE 1-continued

| Cmpd | Structure | Peak absorption (nm) | FWHM (nm) | φ |
| --- | --- | --- | --- | --- |
| SQL-8 | 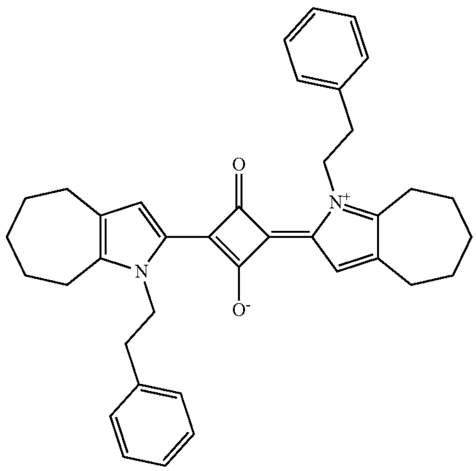 [SMILES: O=C1C(c2cc3c(n2CCc2ccccc2)CCCCC3)=C([O-])/C1=C1\C=C2CCCCCC2=[N+]1CCc1ccccc1] | 587 nm (APC) | 25 nm | |
| SQL-9 | 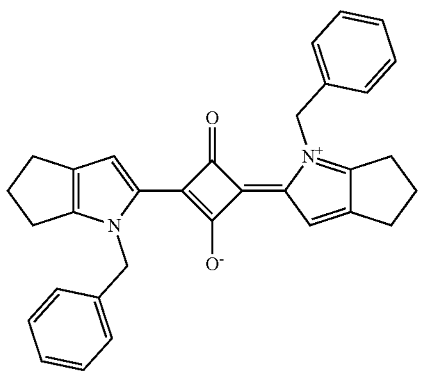 [SMILES: O=C1C(c2cc3c(n2Cc2ccccc2)CCC3)=C([O-])/C1=C1\C=C2CCCC2=[N+]1Cc1ccccc1] | 588 nm (APC) | 25 nm | |
| SQL-10 | 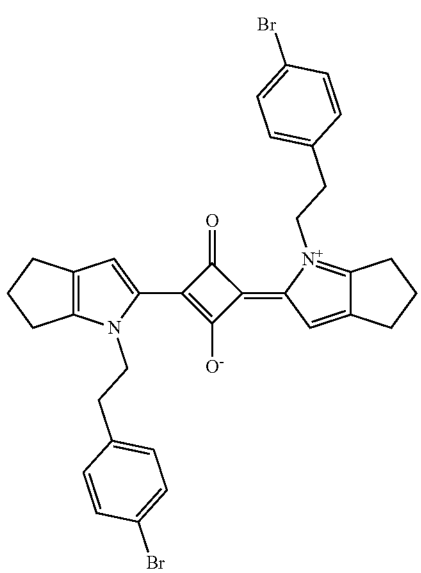 [SMILES: O=C1C(c2cc3c(n2CCc2ccc(Br)cc2)CCC3)=C([O-])/C1=C1\C=C2CCCC2=[N+]1CCc1ccc(Br)cc1] | 588 nm (APC) | 25 nm | |

TABLE 1-continued
| Cmpd | Structure | Peak absorption (nm) | FWHM (nm) | φ |
|---|---|---|---|---|
| SQL-11 | 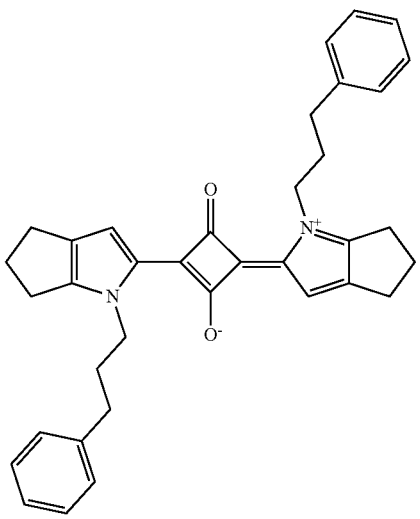 [SMILES: O=C1C(c2cc3c(n2CCCc2ccccc2)CCC3)=C([O-])/C1=C1\C=C2CCCC2=[N+]1CCCc1ccccc1] | 588 nm (APC) | 25 nm | |
| SQL-12 | 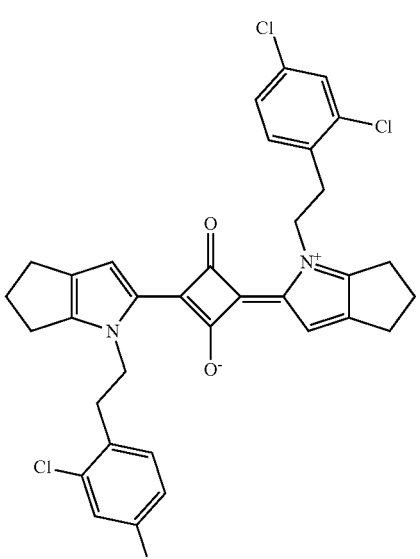 | 589 nm (APC) | 24 nm | |

TABLE 1-continued

| Cmpd | Structure | Peak absorption (nm) | FWHM (nm) | φ |
|---|---|---|---|---|
| SQL-13 | 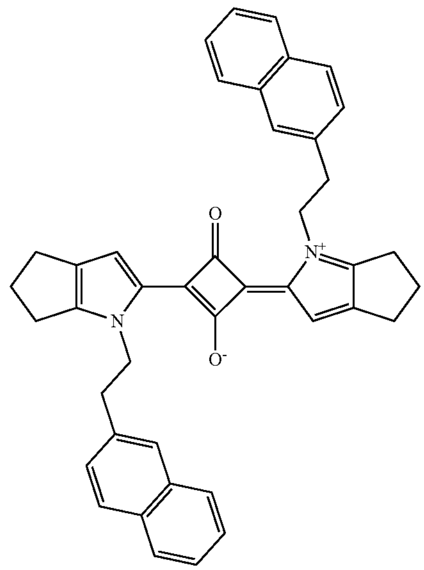 [SMILES: O=C1C(c2cc3c(n2CCc2ccc4ccccc4c2)CCC3)=C([O-])/C1=C1\C=C2CCCC2=[N+]1CCc1ccc2ccccc2c1] | 592 nm (APC) | 26 nm | |
| SQL-14 | 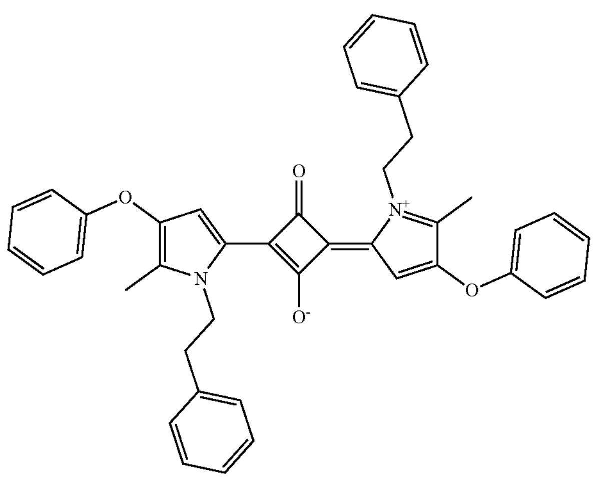 [SMILES: CC1=[N+](CCc2ccccc2)/C(=C2\C(=O)C(c3cc(Oc4ccccc4)c(C)n3CCc3ccccc3)=C2[O-])C=C1Oc1ccccc1] | 591 nm (APC) | 36 nm | |
| SQL-15 | 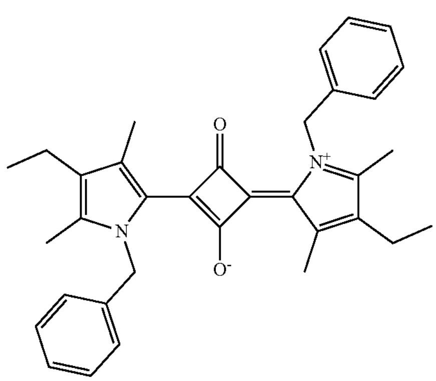 [SMILES: CCC1=C(C)/C(=C2/C(=O)C(c3c(C)c(CC)c(C)n3Cc3ccccc3)=C2[O-])[N+](Cc2ccccc2)=C1C] | 595 nm (APC) | 33 nm | |

TABLE 1-continued

| Cmpd | Structure | Peak absorption (nm) | FWHM (nm) | φ |
|---|---|---|---|---|
| SQL-16 | 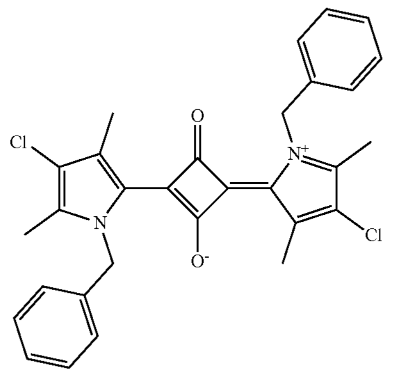 [SMILES: CC1=C(Cl)C(C)=[N+](Cc2ccccc2)/C1=C1\C(=O)C(c2c(C)c(Cl)c(C)n2Cc2ccccc2)=C1[O-]] | 597 nm (APC) | 34 nm | |
| SQL-17 | 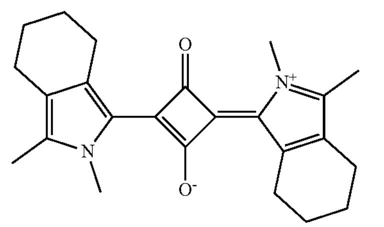 | 599 nm (APC) | 35 nm | |
| SQL-18 | 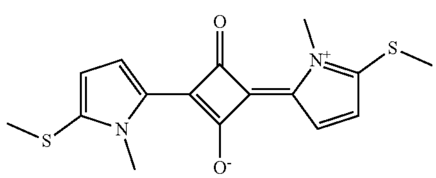 | 614 nm (APC) | 42 nm | |
| SQL-19 | 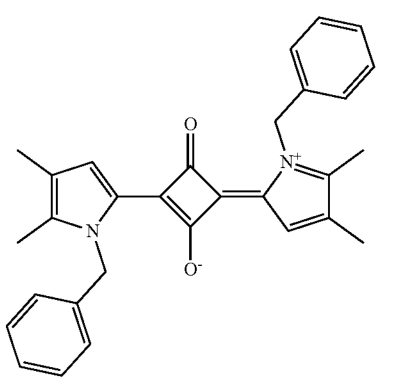 [SMILES: CC1=C/C(=C2/C(=O)C(c3cc(C)c(C)n3Cc3ccccc3)=C2[O-])[N+](Cc2ccccc2)=C1C] | 581 nm (APC) | 26 nm | |

TABLE 1-continued

| Cmpd | Structure | Peak absorption (nm) | FWHM (nm) | φ |
|---|---|---|---|---|
| SQL-20 | 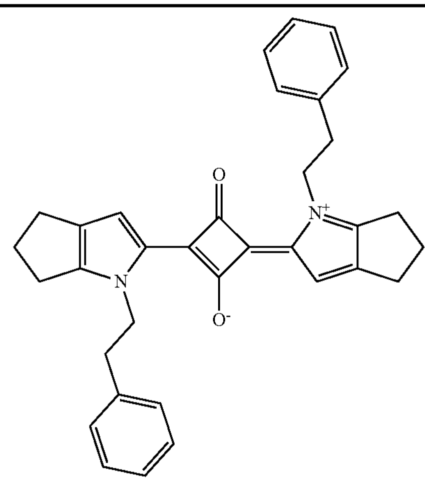 | 591 nm (APC) | 25 nm | |
| SQL-21 | 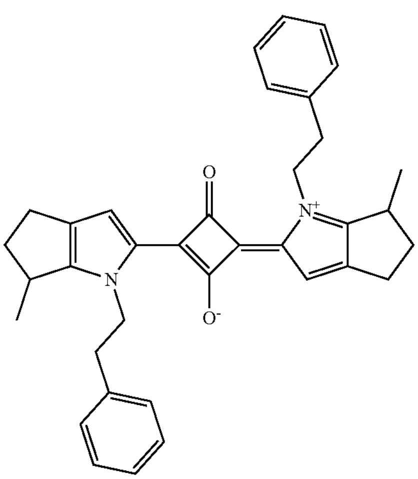 [SMILES: CC1CCC2=C/C(=C3/C(=O)C(c4cc5c(n4CCc4ccccc4)C(C)CC5)=C3[O-])[N+](CCc3ccccc3)=C21] | 593 nm (APC) | 25 | 0.382 |
| SQL-22 | 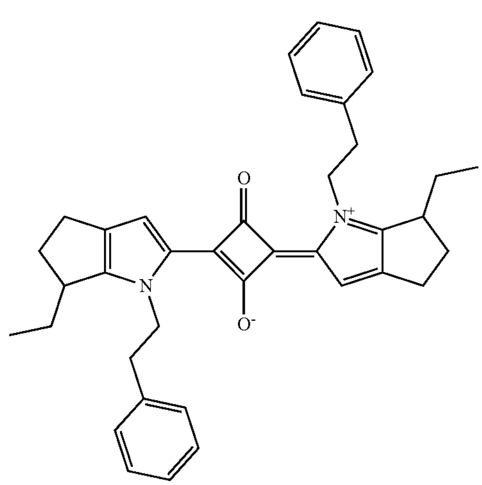 [SMILES: CCC1CCC2=C/C(=C3/C(=O)C(c4cc5c(n4CCc4ccccc4)C(CC)CC5)=C3[O-])[N+](CCc3ccccc3)=C21] | 594 nm (APC) | 25 | 0.129 |

TABLE 1-continued

| Cmpd | Structure | Peak absorption (nm) | FWHM (nm) | φ |
|---|---|---|---|---|
| SQL-23 | 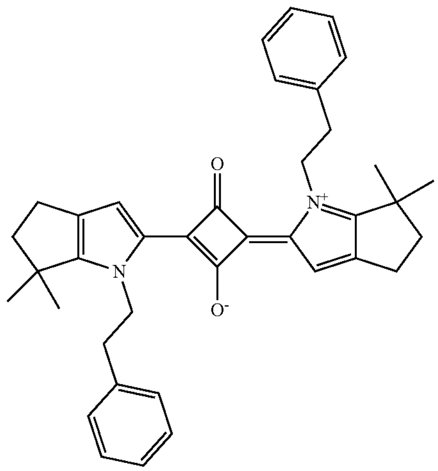 | 594 nm (APC) | 24 nm | 0.197 |
| SQL-24 | 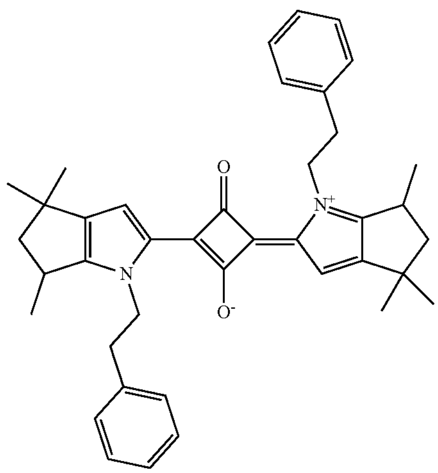 | 592 nm | 25 nm | 0.488 |
| SQL-25 | 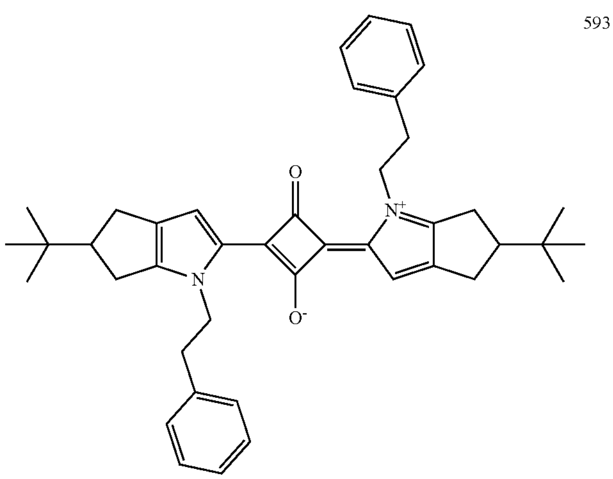 | 593 nm | 24 nm | 0.120 |

TABLE 1-continued

| Cmpd | Structure | Peak absorption (nm) | FWHM (nm) | φ |
|---|---|---|---|---|
| SQL-26 | 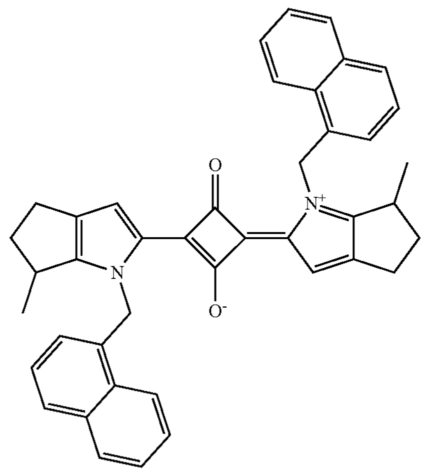 [SMILES: CC1CCC2=C/C(=C3/C(=O)C(c4cc5c(n4Cc4cccc6ccccc46)C(C)CC5)=C3[O-])[N+](Cc3cccc4ccccc34)=C21] | 594 nm | 23 nm | |
| SQL-27 | 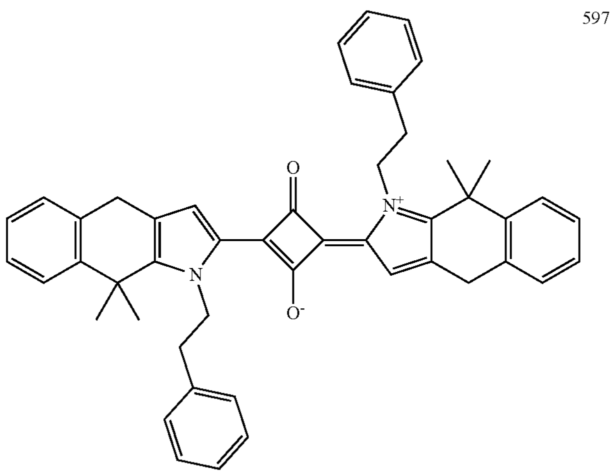 | 597 nm | 27 nm | |
| SQL-28 | 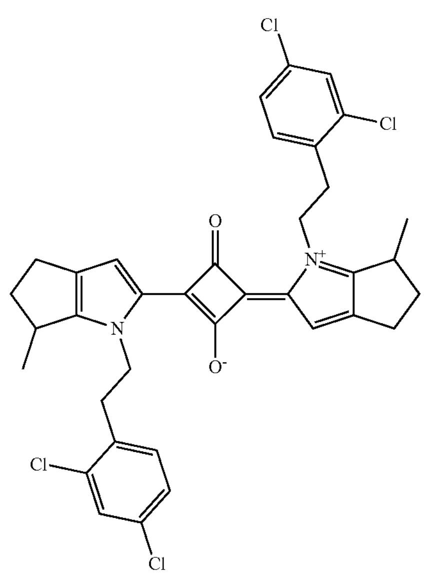 [SMILES: CC1CCC2=C/C(=C3/C(=O)C(c4cc5c(n4CCc4ccc(Cl)cc4Cl)C(C)CC5)=C3[O-])[N+](CCc3ccc(Cl)cc3Cl)=C21] | 594 nm | 24 nm | 0.233 |

What is claimed is:

1. A squarylium compound having the chemical formula:

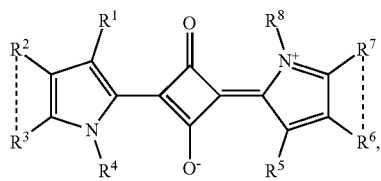

wherein $R^1$, $R^2$, $R^3$, $R^5$, $R^6$, and $R^7$ are independently H, optionally substituted $C_{1-24}$ hydrocarbyl, halogen, optionally substituted $C_{1-24}$—S-hydrocarbyl, or optionally substituted $C_{1-24}$—O-hydrocarbyl; and wherein $R^4$ and $R^8$ are independently H or optionally substituted $C_{1-24}$ hydrocarbyl; and wherein the dashed line represents the presence of a covalent bond.

2. The squarylium compound of claim 1, wherein $R^4$ and $R^8$ are optionally substituted $C_{1-24}$ hydrocarbyl.

3. The squarylium compound of claim 1, wherein $R^2$ and $R^3$ are covalently bound to form an optionally substituted ring structure, and wherein $R^6$ and $R^7$ are covalently bound to form an optionally substituted 5-membered, 6-membered, or 7-membered ring structure.

4. The squarylium compound of claim 3, wherein the optionally substituted ring structure formed is an optionally substituted 5-membered ring.

5. The squarylium compound of claim 3, wherein the compound comprises:

SQL-9

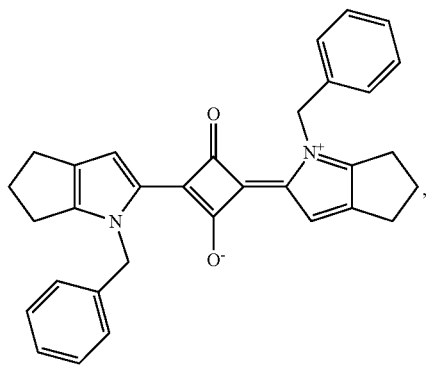

SQL-10

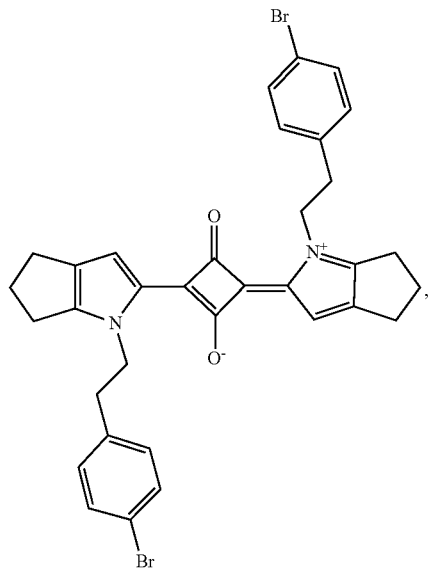

SQL-11

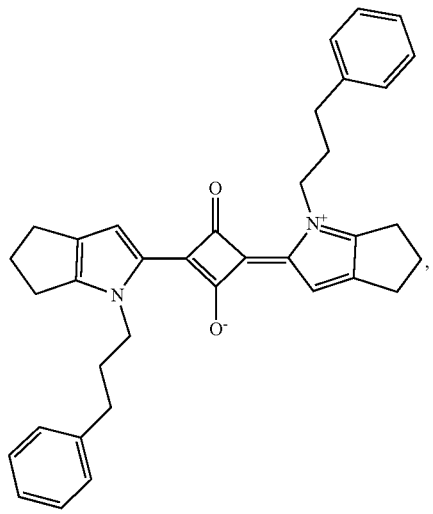

SQL-12

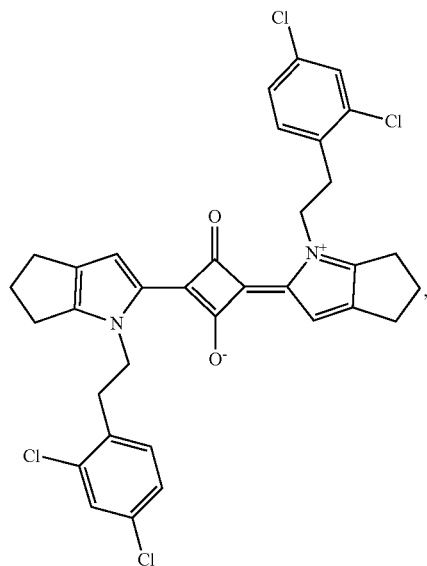

SQL-13
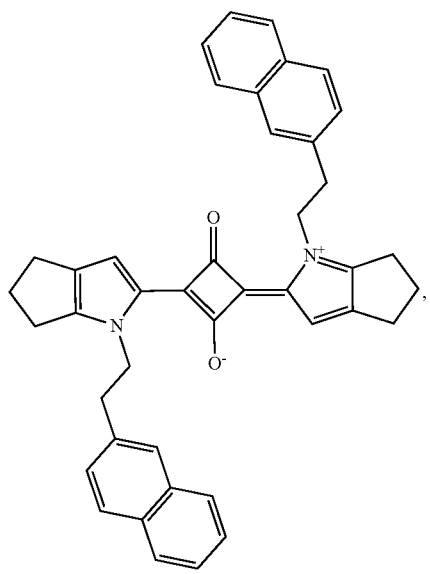
SQL-20
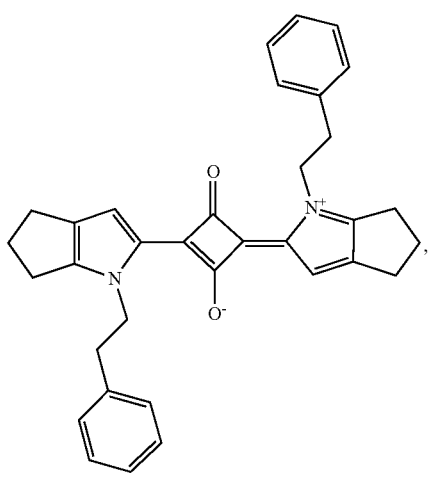
SQL-21
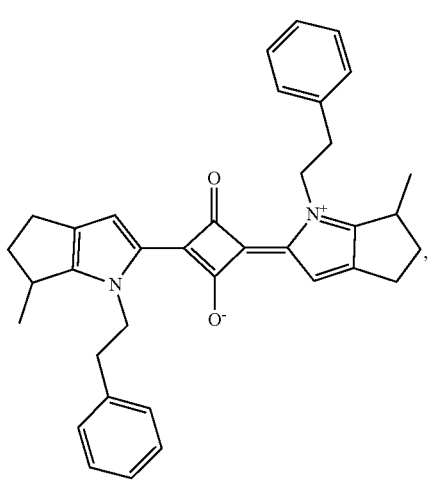
SQL-22
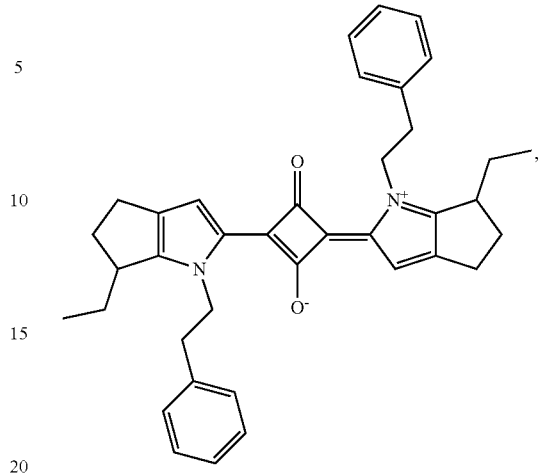
SQL-23
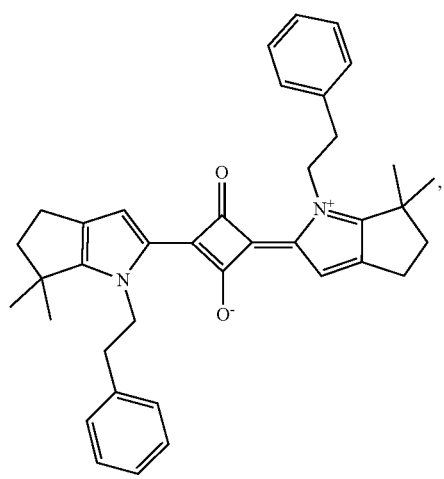
SQL-24
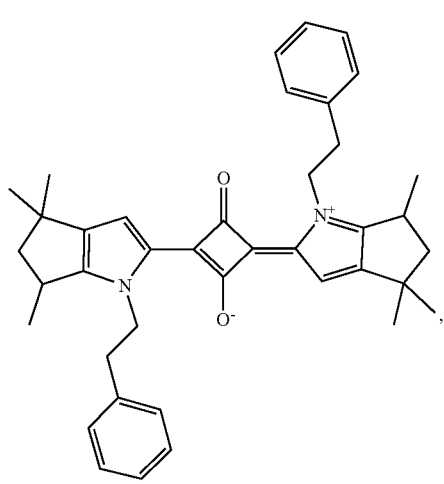

-continued

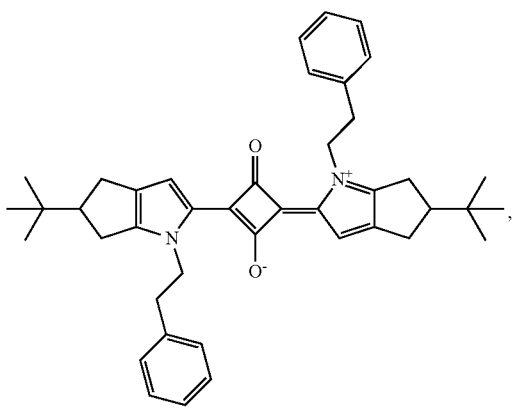
SQL-25

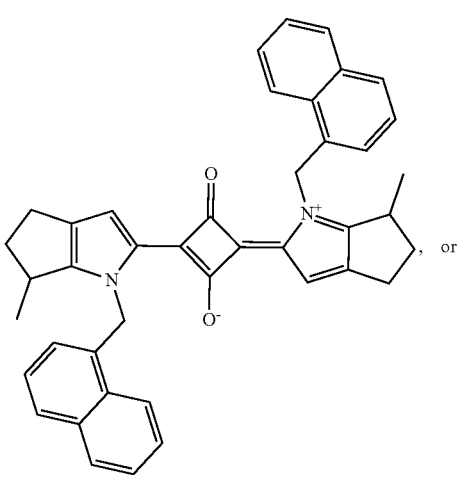
SQL-26

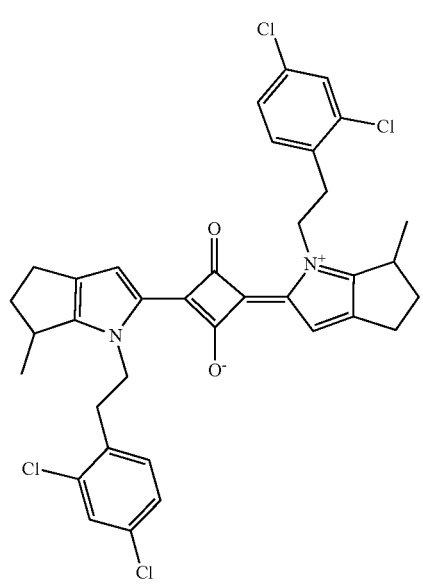
SQL-28 or a combination thereof.

6. The squarylium compound of claim 3, wherein the optionally substituted ring structure formed is an optionally substituted 6-membered ring.

7. The squarylium compound of claim 6, wherein the compound comprises:

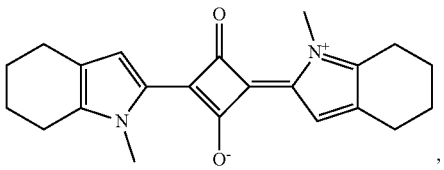
SQL-3

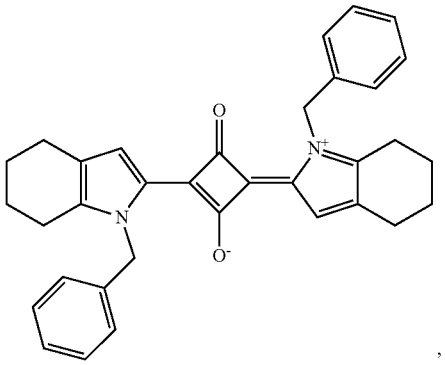
SQL-4

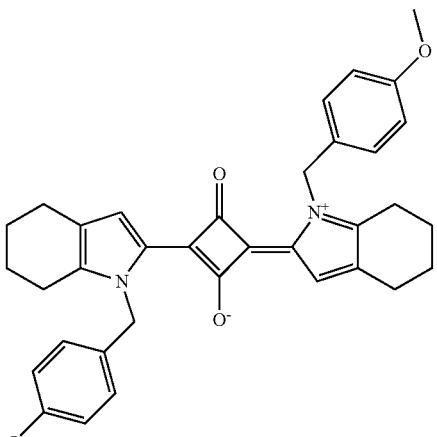
SQL-5

, or

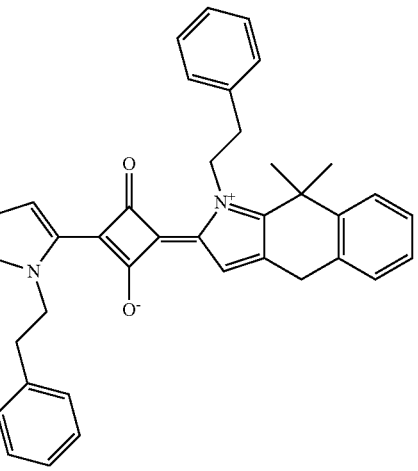
SQL-27 or a combination thereof.

8. The squarylium compound of claim 3, wherein the optionally substituted ring structure formed is an optionally substituted 7-membered ring.

9. The squarylium compound of claim 8, wherein the compound is:

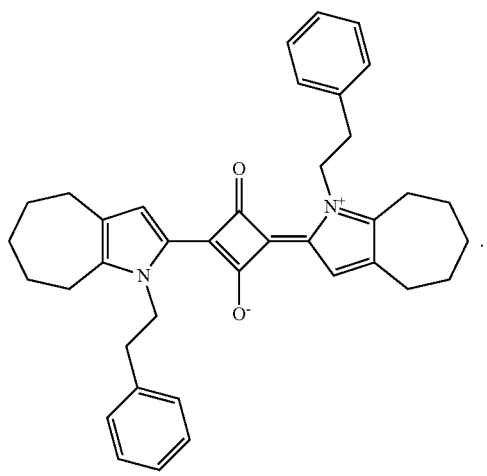

SQL-8

10. The squarylium compound of claim 1, wherein the maximum absorption is in a range of about 550 nm to about 630 nm.

11. The squarylium compound of claim 1, wherein the maximum absorption is in a range of about 580 nm to about 610 nm.

12. The squarylium compound of claim 1, wherein the absorption band's full width at half maximum (FWHM) is 40 nm or less.

13. The squarylium compound of claim 1, wherein the absorption band's full width at half maximum (FWHM) is about 20 nm to about 40 nm.

14. A filter comprising the squarylium compound of claim 1.

15. A display element comprising the filter of claim 14.

* * * * *